(12) United States Patent
Liang et al.

(10) Patent No.: US 7,794,656 B2
(45) Date of Patent: Sep. 14, 2010

(54) DEVICE FOR HANDLING AND ANALYSIS OF A BIOLOGICAL SAMPLE

(75) Inventors: Greg Liang, Cucamonga, CA (US); Kevin J. Kirby, Valley Center, CA (US)

(73) Assignee: Quidel Corporation, San Diego, CA (US)

( * ) Notice: Subject to any disclaimer, the term of this patent is extended or adjusted under 35 U.S.C. 154(b) by 153 days.

(21) Appl. No.: 12/150,148

(22) Filed: Apr. 25, 2008

(65) Prior Publication Data

US 2009/0004058 A1  Jan. 1, 2009

Related U.S. Application Data

(63) Continuation-in-part of application No. 11/625,813, filed on Jan. 22, 2007.

(60) Provisional application No. 60/761,580, filed on Jan. 23, 2006.

(51) Int. Cl.
*G01N 33/00* (2006.01)
*G01N 33/48* (2006.01)
*G01N 21/00* (2006.01)

(52) U.S. Cl. .................... 422/68.1; 435/287.7; 422/56; 422/58; 422/61

(58) Field of Classification Search ................. 422/68.1
See application file for complete search history.

(56) References Cited

U.S. PATENT DOCUMENTS

| | | |
|---|---|---|
| 3,660,033 A | 5/1972 | Schwarz |
| 3,992,158 A | 11/1976 | Przybylowicz et al. |
| 4,275,149 A | 6/1981 | Litman et al. |
| 4,299,916 A | 11/1981 | Litman et al. |
| 4,353,868 A | 10/1982 | Joslin et al. |
| 4,366,241 A | 12/1982 | Tom et al. |
| 4,373,932 A | 2/1983 | Gribnau et al. |
| 4,426,451 A | 1/1984 | Columbus |
| 4,587,099 A | 5/1986 | Rothe et al. |
| 4,632,901 A | 12/1986 | Valkirs et al. |
| 4,643,560 A | 2/1987 | Morse |

(Continued)

FOREIGN PATENT DOCUMENTS

EP  0 249 418 A2  12/1987

(Continued)

OTHER PUBLICATIONS

The International Search report and Written Opinion for PCT Application PCT/US2007/001678, 8 pages, Search Report dated Sep. 26, 2007 (2007).

(Continued)

*Primary Examiner*—Jill Warden
*Assistant Examiner*—Jennifer Wecker
(74) *Attorney, Agent, or Firm*—Judy M. Mohr; LeeAnn Gorthey; King & Spalding LLP

(57) ABSTRACT

An apparatus for detection of an analyte of interest in a solid, semi-solid, or liquid biological sample, using a lateral flow assay test strip, is described. The apparatus minimizes sample handling and manipulation upon introduction of the sample into a sample-receiving chamber and transfer of the sample to a test chamber containing the assay strip.

25 Claims, 16 Drawing Sheets

U.S. PATENT DOCUMENTS

| | | | |
|---|---|---|---|
| 4,695,554 A | 9/1987 | O'Connell et al. |
| 4,702,017 A | 10/1987 | Leinhardt |
| 4,703,017 A | 10/1987 | Campbell et al. |
| 4,806,311 A | 2/1989 | Greenquist |
| 4,824,640 A | 4/1989 | Hildebrand et al. |
| 4,863,875 A | 9/1989 | Bailey et al. |
| 4,916,056 A | 4/1990 | Brown, III et al. |
| 4,943,522 A | 7/1990 | Eisinger et al. |
| 4,945,205 A | 7/1990 | Litman et al. |
| 4,999,285 A | 3/1991 | Stiso |
| 5,008,080 A | 4/1991 | Brown, III et al. |
| 5,075,078 A | 12/1991 | Osikowicz et al. |
| 5,096,837 A | 3/1992 | Fan et al. |
| 5,110,550 A | 5/1992 | Schtipfenbacher et al. |
| 5,120,643 A | 6/1992 | Ching et al. |
| 5,145,789 A | 9/1992 | Corti et al. |
| 5,149,622 A | 9/1992 | Brown et al. |
| 5,160,021 A | 11/1992 | Sibley et al. |
| 5,160,701 A | 11/1992 | Brown, III et al. |
| 5,208,166 A | 5/1993 | Saunders et al. |
| 5,223,220 A | 6/1993 | Fan et al. |
| 5,266,497 A | 11/1993 | Imai et al. |
| 5,268,148 A | 12/1993 | Seymour |
| 5,275,785 A | 1/1994 | May et al. |
| 5,283,038 A | 2/1994 | Seymour |
| 5,338,513 A | 8/1994 | Schtipfenbacher et al. |
| 5,356,782 A | 10/1994 | Moorman et al. |
| 5,401,667 A | 3/1995 | Koike |
| 5,415,994 A | 5/1995 | Imrich et al. |
| 5,458,852 A | 10/1995 | Buechler |
| 5,468,647 A | 11/1995 | Skold et al. |
| 5,504,013 A | 4/1996 | Senior |
| 5,516,644 A | 5/1996 | Yamauchi et al. |
| 5,521,102 A | 5/1996 | Boehringer et al. |
| 5,571,726 A | 11/1996 | Brooks, Jr. et al. |
| 5,591,645 A | 1/1997 | Rosenstein |
| 5,602,040 A | 2/1997 | May et al. |
| 5,622,871 A | 4/1997 | May et al. |
| 5,624,809 A | 4/1997 | Skold et al. |
| 5,656,503 A | 8/1997 | May et al. |
| 5,712,170 A | 1/1998 | Kouvonen et al. |
| 5,712,172 A | 1/1998 | Huang et al. |
| 5,714,389 A | 2/1998 | Charlton et al. |
| 5,726,010 A | 3/1998 | Clark |
| 5,763,262 A | 6/1998 | Wong et al. |
| 5,766,961 A | 6/1998 | Pawlak et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,800,779 A * | 9/1998 | Johnson ...................... 422/58 |
| 5,804,452 A | 9/1998 | Pronovost et al. |
| 5,827,675 A | 10/1998 | Skiffington et al. |
| 5,877,028 A | 3/1999 | Chandler et al. |
| 5,885,527 A | 3/1999 | Buechler |
| 5,895,765 A | 4/1999 | Rheinheimer et al. |
| 5,962,333 A | 10/1999 | Incorvia et al. |
| 5,965,458 A | 10/1999 | Kouvonen et al. |
| 5,989,921 A | 11/1999 | Charlton et al. |
| 5,998,156 A | 12/1999 | Sugiyama |
| 6,019,944 A | 2/2000 | Buechler |
| 6,057,166 A | 5/2000 | Childs et al. |
| 6,087,184 A | 7/2000 | Magginetti et al. |
| 6,109,944 A | 8/2000 | Buechler |
| 6,113,855 A | 9/2000 | Buechler |
| 6,120,733 A | 9/2000 | Goodman et al. |
| 6,143,576 A | 11/2000 | Buechler |
| 6,156,270 A | 12/2000 | Buechler |
| 6,165,798 A | 12/2000 | Brooks |
| 6,180,417 B1 | 1/2001 | Hajizadeh et al. |
| 6,187,268 B1 | 2/2001 | Albarella et al. |
| 6,187,369 B1 | 2/2001 | Beavers |
| 6,194,221 B1 | 2/2001 | Rehg et al. |
| 6,194,222 B1 | 2/2001 | Buechler et al. |
| 6,207,113 B1 | 3/2001 | Kagaya |
| 6,210,898 B1 | 4/2001 | Bouma et al. |
| 6,228,658 B1 | 5/2001 | Fornica et al. |
| 6,228,660 B1 | 5/2001 | May et al. |
| 6,248,294 B1 | 6/2001 | Nason |
| 6,271,040 B1 | 8/2001 | Buechler |
| 6,284,198 B1 | 9/2001 | Kirollos et al. |
| 6,297,060 B1 | 10/2001 | Nowakowski et al. |
| 6,316,205 B1 | 11/2001 | Guan et al. |
| 6,352,862 B1 | 3/2002 | Davis et al. |
| 6,391,265 B1 | 5/2002 | Buechler et al. |
| 6,399,398 B1 | 6/2002 | Cunningham et al. |
| 6,406,920 B1 | 6/2002 | Davis et al. |
| 6,410,341 B1 | 6/2002 | Freitag et al. |
| 6,436,722 B1 | 8/2002 | Clark et al. |
| 6,485,982 B1 | 11/2002 | Charlton |
| 6,534,320 B2 | 3/2003 | Ching et al. |
| 6,537,505 B1 * | 3/2003 | LaBudde et al. ............. 422/103 |
| 6,548,019 B1 | 4/2003 | Lee et al. |
| 6,605,476 B2 | 8/2003 | Kobayashi |
| 6,613,405 B1 | 9/2003 | Hekal |
| 6,656,744 B2 | 12/2003 | Pronovost et al. |
| 6,656,745 B1 | 12/2003 | Cole |
| 6,663,833 B1 | 12/2003 | Stave et al. |
| 6,669,907 B1 | 12/2003 | Buechler |
| 6,673,628 B2 | 1/2004 | Freitag et al. |
| RE38,430 E | 2/2004 | Rosenstein |
| 6,686,170 B1 | 2/2004 | Flanders et al. |
| 6,689,317 B1 | 2/2004 | Rees |
| 6,699,722 B2 | 3/2004 | Bauer et al. |
| 6,726,879 B2 | 4/2004 | Ng et al. |
| 6,730,494 B1 | 5/2004 | Toranto et al. |
| 6,737,278 B1 | 5/2004 | Carlsson et al. |
| 6,780,160 B2 | 8/2004 | Zhou et al. |
| 6,805,837 B2 | 10/2004 | Tydings |
| 6,855,561 B2 | 2/2005 | Jerome et al. |
| 6,921,370 B2 | 7/2005 | Zhou et al. |
| 6,924,153 B1 | 8/2005 | Boehringer et al. |
| 7,005,459 B2 | 2/2006 | Hekal |
| 7,163,514 B2 | 1/2007 | Zhou et al. |
| 7,485,262 B2 * | 2/2009 | DiCesare et al. .............. 422/61 |
| 7,550,112 B2 * | 6/2009 | Gou et al. ..................... 422/58 |
| 2002/0086436 A1 | 7/2002 | Buechler |
| 2002/0098532 A1 | 7/2002 | Yee |
| 2003/0035758 A1 | 2/2003 | Buechler et al. |
| 2003/0157699 A1 | 8/2003 | Jerome et al. |
| 2003/0161762 A1 | 8/2003 | Caron et al. |
| 2003/0211634 A1 | 11/2003 | Jerome et al. |
| 2004/0002165 A1 | 1/2004 | Buchanan et al. |
| 2004/0059256 A1 * | 3/2004 | Perez ........................ 600/583 |
| 2004/0077103 A1 | 4/2004 | Buechler |
| 2004/0152207 A1 | 8/2004 | Nelson et al. |
| 2005/0048670 A1 | 3/2005 | Wu et al. |
| 2005/0119589 A1 | 6/2005 | Tung et al. |
| 2005/0163660 A1 | 7/2005 | Wang |
| 2005/0181518 A1 | 8/2005 | Chandler |
| 2005/0227371 A1 | 10/2005 | Gokhan |
| 2006/0029517 A1 | 2/2006 | Hartselle |
| 2006/0062690 A1 * | 3/2006 | Lawrence .................... 422/58 |
| 2006/0078986 A1 | 4/2006 | Ly et al. |
| 2006/0210448 A1 | 9/2006 | Wang et al. |
| 2007/0065339 A1 | 3/2007 | Huff |
| 2007/0092402 A1 | 4/2007 | Wu et al. |
| 2007/0275475 A1 | 11/2007 | Liang |
| 2008/0019867 A1 | 1/2008 | Johnson et al. |
| 2008/0272283 A1 * | 11/2008 | Feldsine et al. ............. 250/229 |

FOREIGN PATENT DOCUMENTS

| | | |
|---|---|---|
| EP | 0 258 963 A2 | 3/1988 |
| EP | 0 260 965 A2 | 3/1988 |

| | | |
|---|---|---|
| EP | 0 353 500 A2 | 2/1990 |
| EP | 0 383 819 B1 | 4/1997 |
| EP | 0 903 584 A1 | 3/1999 |
| EP | 1 046 913 A2 | 10/2000 |
| EP | 1 046 913 A3 | 10/2000 |
| EP | 1 174 716 A2 | 1/2002 |
| EP | 1 174 716 A3 | 1/2002 |
| EP | 1 248 112 A2 | 10/2002 |
| EP | 0 833 157 A1 | 11/2002 |
| EP | 0 291 194 B2 | 7/2003 |
| EP | 1 327 884 A1 | 7/2003 |
| EP | 0 901 630 B1 | 8/2003 |
| EP | 1 376 131 A1 | 1/2004 |
| EP | 1 754 971 A1 | 2/2007 |
| GB | 2404735 A | 2/2005 |
| WO | WO88/08534 A1 | 11/1988 |
| WO | WO89/04156 A1 | 5/1989 |
| WO | WO92/21977 A1 | 12/1992 |
| WO | WO95/13542 A1 | 5/1995 |
| WO | WO97/06437 A1 | 2/1997 |
| WO | WO97/26083 A1 | 7/1997 |
| WO | WO97/44664 A1 | 11/1997 |
| WO | WO99/47930 A1 | 9/1999 |
| WO | WO00/63697 A1 | 10/2000 |
| WO | WO01/57522 A2 | 8/2001 |
| WO | WO 02/50609 A2 | 6/2002 |
| WO | WO 02/50609 A3 | 6/2002 |
| WO | WO2004/011942 A1 | 2/2004 |
| WO | WO2005/095967 A1 | 10/2005 |
| WO | WO2006/005483 A1 | 1/2006 |
| WO | WO2007/087261 A2 | 8/2007 |
| WO | WO2007/098184 A2 | 8/2007 |
| WO | WO2007/105680 A1 | 9/2007 |
| WO | WO 2009/011869 A1 | 1/2009 |

OTHER PUBLICATIONS

Lindberg, Roy A., "Plastic-Molding Processes", Chapter 10 in *Processes and Materials of Manufacture* $3^{rd}$ ed., Allyn an d Bacon, Boston pp. 393-432 (1983).

Odexxo Company, Product Description from Odexxo Company Website "All-in-One Fecal Sample Collecting Device", http://www.odexxo.com (2008).

The International Search report and Written Opinion for PCT Application PCT/US2009/002542, Search Report dated Jul. 24, 2009, 15 pages (2009).

U.S. Appl. No. 12/390,303, Kirby, Kevin.

Non-final Office Action dated Sep. 16, 2009.

* cited by examiner

FIG. 1A
FIG. 1B
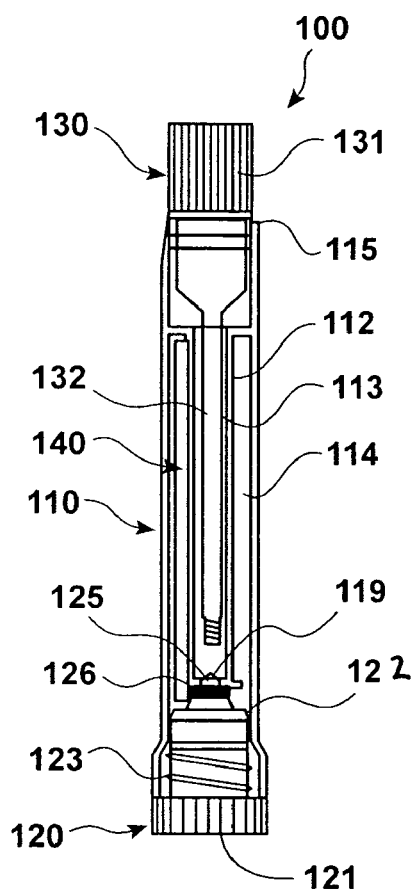
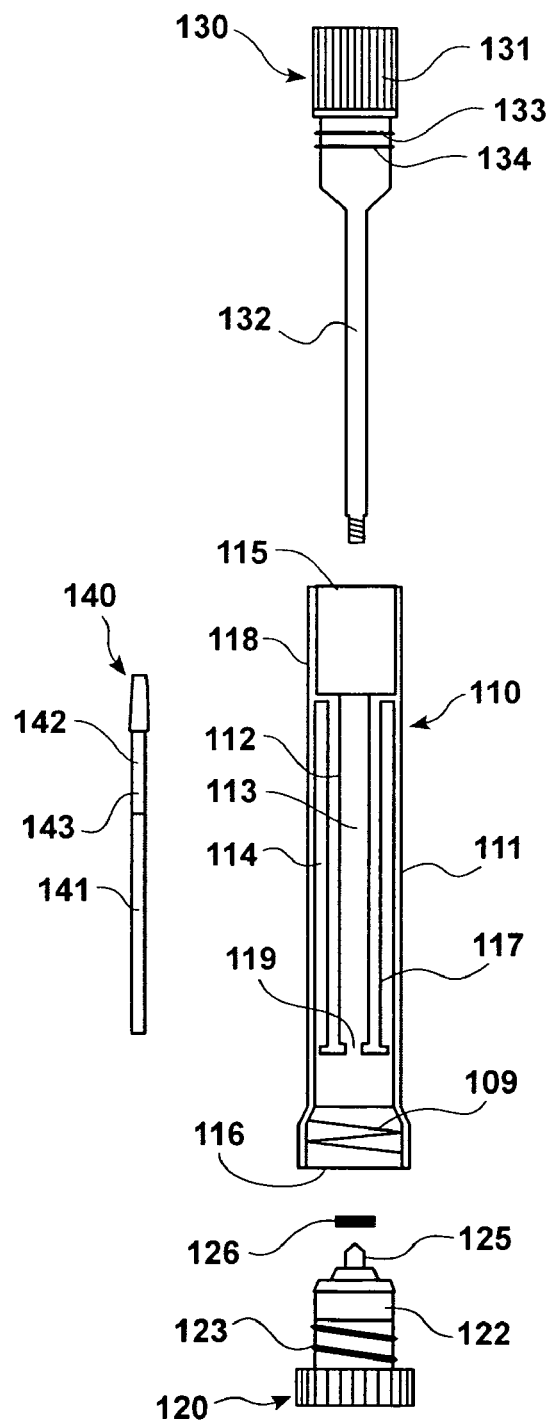

US 7,794,656 B2

DEVICE FOR HANDLING AND ANALYSIS OF A BIOLOGICAL SAMPLE

PRIORITY

The present application is a continuation-in-part application of U.S. application Ser. No. 11/625,813, filed Jan. 22, 2007, and of International Application No. PCT/US2007/001678, filed Jan. 23, 2007, both of which claim the benefit of U.S. provisional application No. 60/761,580, filed Jan. 23, 2006. Each of the priority applications is incorporated by reference herein in its entirety.

TECHNICAL FIELD

The subject matter described relates to an apparatus for an assay, and more particularly to an apparatus comprising a lateral flow assay test strip. The apparatus provides for detection of an analyte in a biological sample, with minimal handling and/or manipulation of the sample.

BACKGROUND

Testing of biological samples, whether in solid, semi-solid, or liquid form, often requires pre-treating the sample with a buffer, typically for dilution, solubilization, or extraction of an analyte in the sample to be detected. For example, biological samples, such as stool, blood, urine, saliva, or swab specimens of the cervix, urethra, nostril, or throat, as well as environmental samples, such as food product samples, soil and dust, are commonly exposed to a buffer or other solution prior to reaction with an analytic reagent and/or detection or measurement of the analyte of interest. Pre-treatment results in a sample solution that is often more suitable than the neat sample for further processing, reaction, and ultimate detection of the analyte of interest.

In a conventional apparatus, the biological sample is mixed with a buffer in a container separate from the test device used to detect the presence, or absence, of a particular analyte. In many testing protocols, a portion or aliquot of the buffer/sample solution is transferred to a second container or location for contact with a reagent to obtain a test result, e.g., a result indicating the presence or absence of an analyte of interest, and, in some tests, its quantity if the analyte is present.

Such conventional prepackaged test devices and kits are prone to user error, particularly by non-laboratory personnel. Untrained users can have difficulty with the multiple steps involved, particularly the requirement of pre-treating the biological sample with a buffer and then transferring an aliquot to a second container. Another disadvantage of conventional test devices is that many do not readily accept solid or semi-solid samples, which require pre-mixing with a buffer prior to reacting with a reagent to obtain a test result.

The need exists in the art for an apparatus in which the steps involved for collection and detection of an analyte in a biological sample can be performed in a single apparatus that is reliable and accurate irrespective of the skill level or training of the user. Moreover, there is a need for an apparatus that minimizes the need for user manipulation of, and contact with, sample by, for example avoiding the need for transfer of a sample aliquot to a separate apparatus for detection of an analyte. An apparatus that provides for sample collection, mixing of the sample with a buffer, reaction of the buffer/sample with an analytical reagent and detection and/or measurement of an analyte in a biological sample is desired.

BRIEF SUMMARY

The following aspects and embodiments thereof described and illustrated below are meant to be exemplary and illustrative, not limiting in scope.

In one aspect, an apparatus for detecting the presence or absence of a substance in a biological sample is provided. The apparatus comprises a test assembly comprising an inner wall defining a sample-receiving chamber, and a median wall that together with the inner wall define a test chamber. The sample-receiving chamber and the test chamber are capable of fluid communication via an opening. An assay test strip, such as, for example, an immunoassay test strip, is disposed in the test chamber, and a base is movably mounted on the test assembly, whereby the base is moveable between a closed position and an open position to achieve movement of a valve dimensioned for engagement with the opening, thereby controlling fluid communication between the sample-receiving chamber and the test chamber. For example, the base may block or seal the opening in the closed position and then be moved into an open position, unblocking/unsealing the opening to permit fluid communication between the chambers.

In one embodiment, the test chamber further comprises at least a first sub-chamber. In other embodiments, the test chamber further comprises two or more sub-chambers.

In another embodiment, the at least first sub-chamber contains a desiccant. In another embodiment, the test chamber contains a lateral flow assay test strip. In yet another embodiment, the test chamber and the sub-chamber each have disposed therein a lateral flow assay test strip for detection of the same or different analytes of interest. In particular embodiments, the assay strip is an immunoassay strip.

In one embodiment, the base attached to the test assembly is rotatably attached, for movement in a radial direction. In another embodiment, the base is movably attached, for lateral or vertical movement away from and toward the test assembly.

In some embodiments, the sample is a solid or semi-solid sample. In particular embodiments, the sample is a stool sample.

In some embodiments, the assay strip is for performing an immunoassay. In particular embodiments, the assay strip comprises at least one antibody.

In some embodiments, the test assembly comprises a transparent portion for viewing the assay strip.

In another aspect, a kit of parts is provided comprising the described apparatus, and instructions for use. The apparatus may include buffer solution within the sample-receiving chamber.

In some embodiments, a kit of parts is provided comprising the described apparatus, instructions for use, and a label for affixing to the apparatus.

In addition to the exemplary aspects and embodiments described above, further aspects and embodiments will become apparent by reference to the drawings and by study of the following descriptions.

BRIEF DESCRIPTION OF THE DRAWINGS

FIG. 1A is a cross-sectional view of an embodiment of an apparatus for use in detecting an analyte in a biological sample;

FIG. 1B is an exploded view of the apparatus of FIG. 1A;

FIG. 3E shows a cross-sectional side view of the base portion, and FIGS. 3F-3G are plan and perspective views, respectively, of the bottom of the base portion;

DETAILED DESCRIPTION

I. Definitions

Figures 2A, 2B, 2C:
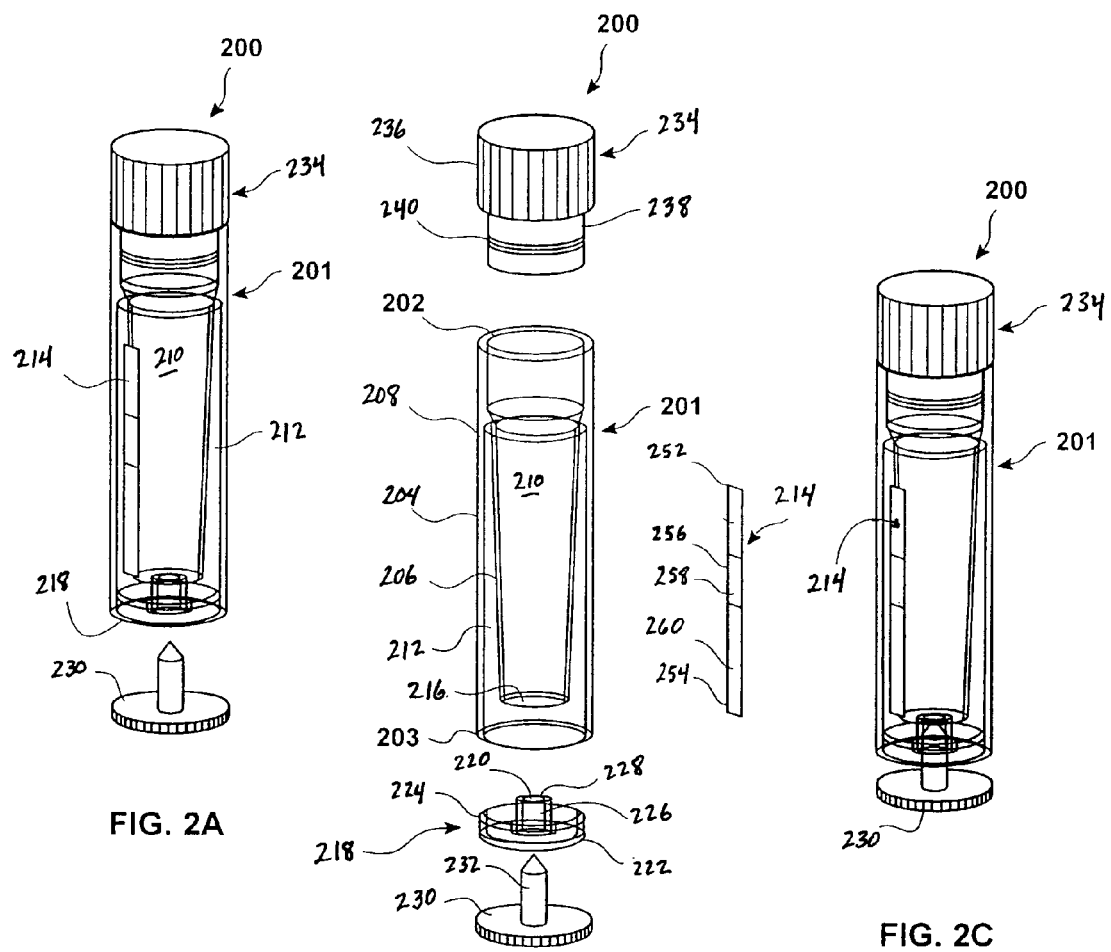
FIG. 2A is a perspective view of another embodiment of an apparatus for use in detecting an analyte in a biological sample.
FIG. 2B is an exploded view of the apparatus of FIG. 2A.
FIG. 2C is a perspective view of the apparatus of FIG. 2A in its test position.

The singular forms "a", "an", and "the" include plural reference unless the context clearly dictates otherwise.

Unless defined otherwise, all technical and scientific terms used herein have the same meanings as commonly understood by one of ordinary skill in the art to which the present subject matter belongs.

Terms of orientation such as "up" and "down" or "top" and "bottom" or "upper" and "lower" and the like refer to orientation of the parts of the device as shown in the drawings, and may or may not be the particular orientation during use.

As used herein, a component is "integral to" another component when the two components are manufactured or assembled as a single piece.

An element or component of the present device is "separate from" another element or component when the two are manufactured as separate pieces.

The term "directly" as used herein intends that one structure is in physical contact with another structure.

"Indirectly" means that one structure is not in immediate physical contact with another structure, but rather contacts one or more intermediary structure(s) that contacts the other structure.

A "lateral flow assay test strip" refers to assay test strips of the type typically found in a lateral flow (or dipstick) assay device. Such test strips include reagents useful for detecting the presence of, or indicating the absence of, or determining the amount of, an analyte in a biological sample. Such test strips permit movement of the sample, or of a liquid solution containing the sample, through a matrix or material, such as a porous or woven material, by lateral (or vertical) flow, typically via capillary or wicking action. Examples of devices comprising lateral flow assay test strips are described, for example, in U.S. Pat. Nos. 5,766,961; 6,656,744; 6,924, 153; 7,179,657; and 6,656,744, and in WO2005/031355, each of which are incorporated by reference herein, in their entirety.

II. Apparatus

An embodiment of an apparatus for detection of an analyte of interest in a biological sample by lateral flow of the sample in an immunoassay device is depicted in FIGS. 1A-1C. FIG. 1A is an illustration of an exemplary apparatus shown in side-view, with the same apparatus shown in exploded side-view in FIG. 1B. With initial reference to FIGS. 1A-1B, device 100 is comprised of an assembly housing 110, base portion 120, an optional cap member 130, and an immunoassay strip 140. Assembly housing 110 is comprised of an exterior wall 111 and an interior (or septum) wall 112 separating the assembly housing into two chambers: a sample receiving chamber 113 and a test chamber 114. Assembly housing 110 has an upper end 115 and a lower end 116. Interior wall 112 has a bottom section 117 and a top section 118. Bottom section 117 of interior wall 112 comprises a port or gap 119, which serves as an opening 119 in the bottom section of sample receiving chamber 113 to permit fluid communication between the sample receiving chamber 113 and test chamber 114. Lower end 116 of exterior wall 111 may have a thread 109 for engaging a corresponding thread in the base 120.

Base 120 comprises a handle section 121, an insert section 122 having, in this embodiment, a thread 123. Base 120 also comprises a plug member 125 sized for contact with and/or insertion into opening 119 of sample receiving chamber 113. An optional sealing member 126, such as a gasket or O-ring seal, is disposed around plug member 125, or optionally around insert section 122, to provide a substantially fluid-tight seal when in the closed position (see, e.g., FIG. 1A). As will be described in more detail below, plug member 125 is movable into and out of opening 119 to modulate flow of liquid from sample receiving chamber 113 to the test chamber 114 in which an assay strip, such as, for example, an immunoassay strip, is disposed.

Apparatus 100 may comprise an optional cap member 130. Cap member 130 is comprised of a handle 131 and sampling member (or sampler) 132. Cap member when inserted into upper end 115 of assembly housing 110 extends into sample receiving chamber 113. Cap member 130 when fully inserted into upper end 115 of assembly housing 110 also serves to seal or close sample receiving chamber 113. One or more optional sealing members 133, 134 can be included to ensure a fluid-tight seal. Sampling member 132 may be used to collect a biological sample and/or to introduce a sample into sample receiving chamber 113.

In a preferred embodiment, apparatus 100 comprises an assay strip (or assay reagent member) 140 adapted for insertion into the test chamber 114. The configuration and components of assay strip 140 can vary depending on the intended application and the analyte of interest. By way of example, assay strip 140 may include a wicking section 141 and a test area 142 that includes one or more assay reagents 143. When a sample solution contacts wick section 141, the sample solution wicks to test area 142 for contact with assay reagent(s) 143. Following appropriate incubation, the presence or quantity of an analyte of interest in the biological sample solution is detected, if present.

As noted above, plug member 125 is movable within opening 119 to modulate flow of liquid from sample receiving chamber 113 to the test chamber 114 in which assay strip 140 is disposed. Movement of plug member 125 is achieved by movement of base 120, which, in the illustrated embodiment, is rotatable in a clock-wise and counter-clockwise direction when thread 109 of assembly housing 111 is engaged with thread 123 of base 120. Base 120 in a fully closed position engages plug member 125 with opening 119 to obstruct opening 119 and prevent fluid transfer therethrough. Base 120, when not in its fully closed position, permits fluid flow through opening 119, where the rate and amount of fluid flow is controllable by the position of the base, and therefore plug member 125. User-controlled movement of base 120 in, for example, a counter-clockwise direction, loosens the fit of base 120 in assembly housing 110, withdraws plug member 125 partially or completely depending on the extent of loosening from opening 119. For example, turning base 120 one-eighth of a turn or one-quarter of a turn, from a fully closed position to a partially open position, may be sufficient to permit escape of fluid held in the sample receiving chamber. In this way, fluid flows from sample receiving chamber 113 to test chamber 114, to contact assay strip 140. An assay result can be read directly from assay strip 140, which may be visible through at least a portion of exterior wall 111 of the assembly housing.

As can be appreciated, the apparatus permits collection of a sample and placement of the sample within the sample receiving chamber, and analysis soon after collection or at a later time. With respect to the latter embodiment, a user is provided with the apparatus as shown in FIG. 1A, with an immunoassay strip inserted into the test chamber, and the base in a fully closed position. The user removes the cap member and collects or places a sample on the sampling member or otherwise adds sample to the sample receiving chamber. By way of example, the sampling member may be configured for swapping or inserting into a solid or semi-solid sample, such as feces, to collect sample material for introduction into the sample receiving chamber. Alternatively, the sampling member may be configured for collecting a nasal, nasopharyngeal, throat, vaginal, cervical or similar mucosal or saliva sample, by, for example comprising a swab at the end of the sampling member distal from the handle/cap member thereof. Once sample is located on the sample receiving member (or otherwise placed within the sample receiving chamber), the cap member is inserted into the assembly housing, to secure the sample within the sample receiving chamber. The sample can be stored inside the sample receiving chamber for analysis at later time, by the user or by a laboratory technician, or other trained personnel. The laboratory technician or other trained personnel may be at a remote location, requiring transport of the apparatus. It will also be appreciated that depending on the sample collected, a buffer or other solution for treating or diluting the biological sample may be present in the sample receiving chamber when the apparatus is provided to the user. That is, the buffer or pretreatment solution is present in the sample receiving chamber prior to introduction of the biological sample into the sample receiving chamber.

Where a biological sample is to be assayed and analyzed shortly after sample collection and introduction to the sample receiving chamber, such as, for example, when an analyte of interest, the sample, or other substance in the apparatus is not stable for a sufficient time period to permit extended transportation or the like, the user can activate the apparatus to initiate sample analysis shortly after placing the sample into the sample receiving chamber. This is accomplished, in the illustrated embodiment (FIGS. 1A and 1B), by turning the base from its fully closed position to a partially closed or fully open position. Fluid flows from the sample receiving chamber to the test chamber via the opening in the lower portion of the housing assembly. The user can observe a result on the assay strip, or can give or ship the activated apparatus to a laboratory technician or other trained person to record the data or interpret the results of the assay. The apparatus may be returned to the closed/inactivated position, or remain in the open/activated position, prior to being given or shipped to trained personnel, depending on the particular assay.

A user may read and interpret the results of the assay without the aid of trained personnel, optionally assisted by written or digitally recorded instructions provided with the apparatus. Reading and interpretation of the results of the assay by the user may be preferred, for example, where results are a matter of privacy (e.g., pregnancy, HIV, paternity tests) or required or desired immediately (e.g., detection of upper respiratory infection, such as flu, cold or the like) for purposes of determining whether to use over-the-counter treatment methods and/or to visit a physician for further diagnosis and/or treatment or where the apparatus is used in laboratory, field, or forensic analysis. Where possible, assays may be designed to provide a detectable signal/result that does not require special training to read and/or interpreted.

In some embodiments, the plug 125 can be omitted from the apparatus, or the base can be maintained in a partially-closed or open position such that the passage between the sample receiving chamber and the test chamber is partially or fully open. When a fluid biological sample is introduced into the sample receiving chamber, a volume of the sample flows from the sample receiving chamber into the test chamber through the opening in the sample receiving chamber. It will be appreciated that this embodiment is suitable, for example, when there is no need to premix the sample with a buffer in the sample receiving chamber and/or it is desirable to introduce the sample immediately to the test chamber.

Other means for permitting fluid communication from the sample-receiving chamber to the test chamber may be employed in the apparatus. For example, the apparatus of FIGS. 1A-1B may be modified such that a hole or port (i.e., a functional equivalent of opening 119) is formed by means of a pin or other sharp edge or protrusion attached to a top surface of base 120. In this manner, a hole is created the when the base is tightened into housing assembly 110, allowing the sample solution to flow from the sample-receiving chamber to the test chamber. Further variations on the valve mechanism are described herein.

FIGS. 2A-2C depict another embodiment of an apparatus, where an apparatus 200 is illustrated prior to use in FIG. 2A, in exploded view in FIG. 2B, and during or after use in FIG. 2C. With reference initially to FIGS. 2A-2B, apparatus 200 comprises an assembly housing 201 having an upper end 202 and a lower end 203. Assembly housing 201 has an exterior wall 204 and interior wall 206 that join together at a neck area 208. Together, the exterior wall and the interior wall form and define a sample receiving chamber 210 and a test chamber 212. Positioned within test chamber 212 is an assay strip or reagent member 214. A breakable seal 216, seen best in FIG. 2B, separates sample receiving chamber 210 from test chamber 212 prior to use. The breakable seal can be fabricated from any number of materials, such as plastics, rubbers, foil, and equivalent material.

An end plug 218 is designed for insertion into lower end 203 of assembly housing 201, to close the sample receiving chamber and the test chamber from the environment. End plug 218 includes an upper end 230 and lower end 222, a sidewall 224 that abuts an interior surface of exterior wall 204 when the end plug is inserted into lower end 203 of the assembly housing, as seen in FIG. 2A. A through hole 226 extends from the end plug, with an optional breakable seal 228 at upper end 220.

A piercing element, such as a pincap 230, can optionally be provided with the apparatus for piercing optional breakable seal 228 when present and for piercing breakable seal 216. Puncture of breakable seal 216 brings the sample receiving chamber in fluid communication with the test chamber, and enables liquid flow between the two chambers. The piercing element 230 comprises a rod 232 dimensioned for insertion into through hole 226 of end plug 218, as seen in FIG. 2C, and for piercing frangible seals 228 and/or 216.

An optional cap 234 is designed for insertion into upper end 202 of test assembly 201. Cap 234 comprises a handle section 236 and an insert section 238 sized to fit into the opening at the upper end 202 of assembly housing 201. The cap may include a thread 240 that engages a corresponding thread (not seen) on the assembly housing or that is comprised of a material that sealably engages the inner wall of the upper end 202 of the housing. The thread on the apparatus may be a female thread, allowing the cap to fit inside the assembly housing or a male thread, allowing the cap to fit over the assembly housing. Alternatively, the cap may include one or more sealing members, such as an O-ring or gasket, to sealingly engage the assembly housing with a fluid-tight seal.

Assay test strip 214 may comprise an upper end 252, a lower end 254, a test area 256 comprised of one or more assay reagents 258, and a wick section 260. Wick section 260 assists in transfer of a liquid sample to test area 256. Assay strip 214 is preferably disposed inside test chamber 212 with upper end 252 oriented towards upper end 202 of assembly housing.

In use, a device as depicted in FIG. 2A is provided to a user. The user removes the cap and places a biological sample into the sample receiving chamber. Depending on the intended use and/or state of the biological sample, a buffer or pretreatment solution may be present in the sample receiving chamber of the device when provided to the user, or the user can charge the sample receiving chamber with such a solution. For example, if the biological sample is a solid, is in dried form, or is contained on or within a material, tissue, or fabric, a buffer or pretreatment solution is typically preloaded into the sample receiving chamber to solubilize the biological sample. After placing the biological sample into the sample receiving chamber, the cap is secured in place, and the device can be shaken if desired or needed to assist in solubilzing or premixing the sample with any solution in the sample receiving chamber. Then, the user pierces the frangible seal or seals so that the sample receiving chamber and the test chamber containing the immunoassay test strip are in fluid communication. This step is illustrated in FIG. 2C, where a user inserts the pin cap into the end plug of the device. It will be appreciated that any sharp object of an appropriate size can be inserted into the device to pierce the frangible seal(s), such as a safety pin, needle, toothpick, paper clip end, or the like. The piercing means may be sanitary or sterile, so as not to contaminate the specimen or sample solution. Upon piercing the frangible seal, fluid flows from the sample receiving chamber to the test chamber, and contacts the immunoassay test strip. As discussed above with reference to FIGS. 1A-1B, the test strip can be analyzed or interpreted by the user or by laboratory personnel at the test site or a remote location by transport of the device. It will also be appreciated that after placement of the biological sample in the sample receiving chamber, the device can be stored for later piercing of the breakable seal to bring the sample in contact with the immunoassay test strip at a later time.

Figure 3A:
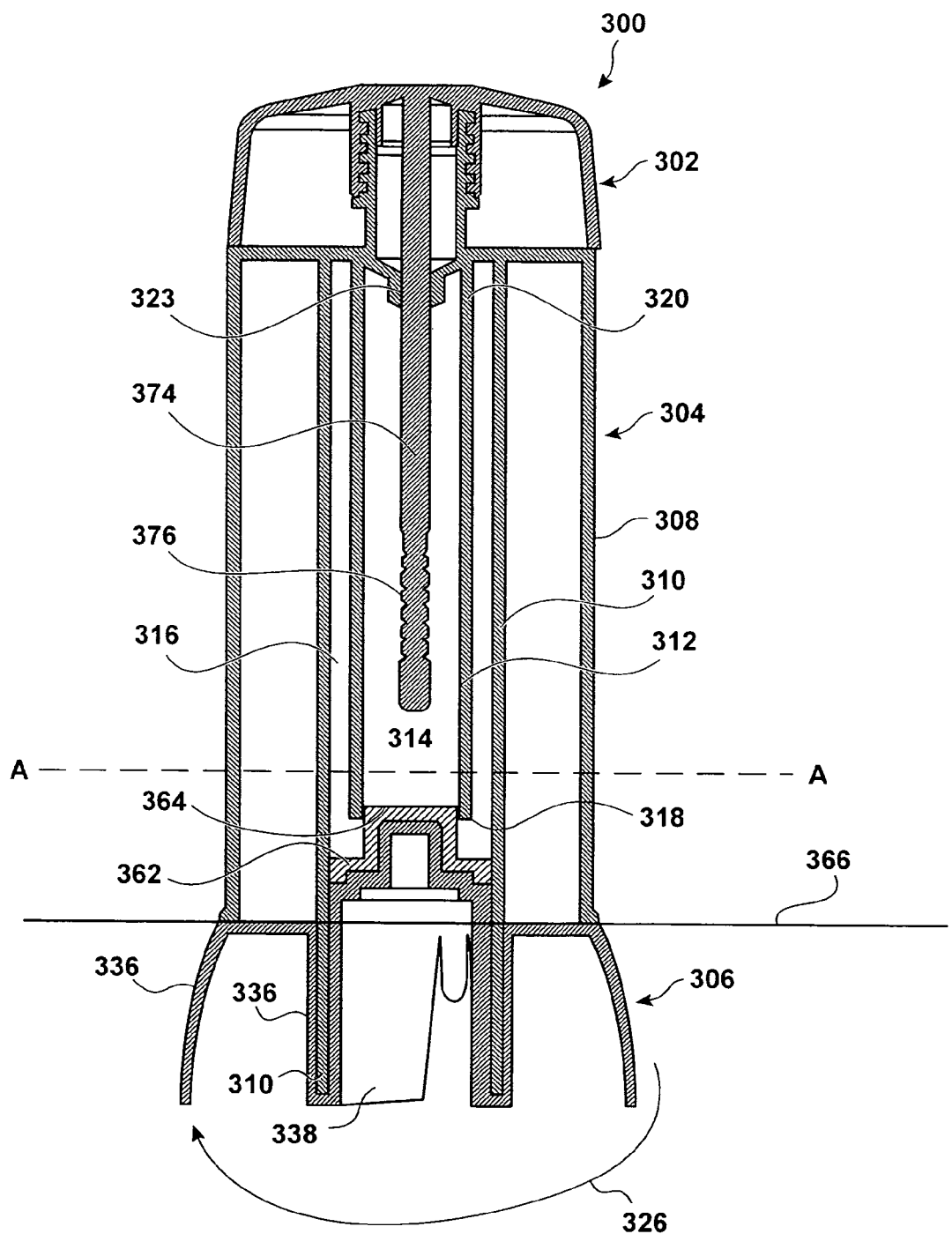
FIG. 3A is a cross-sectional view of another embodiment of an apparatus for use in detecting an analyte in a biological sample.
Figure 3B:
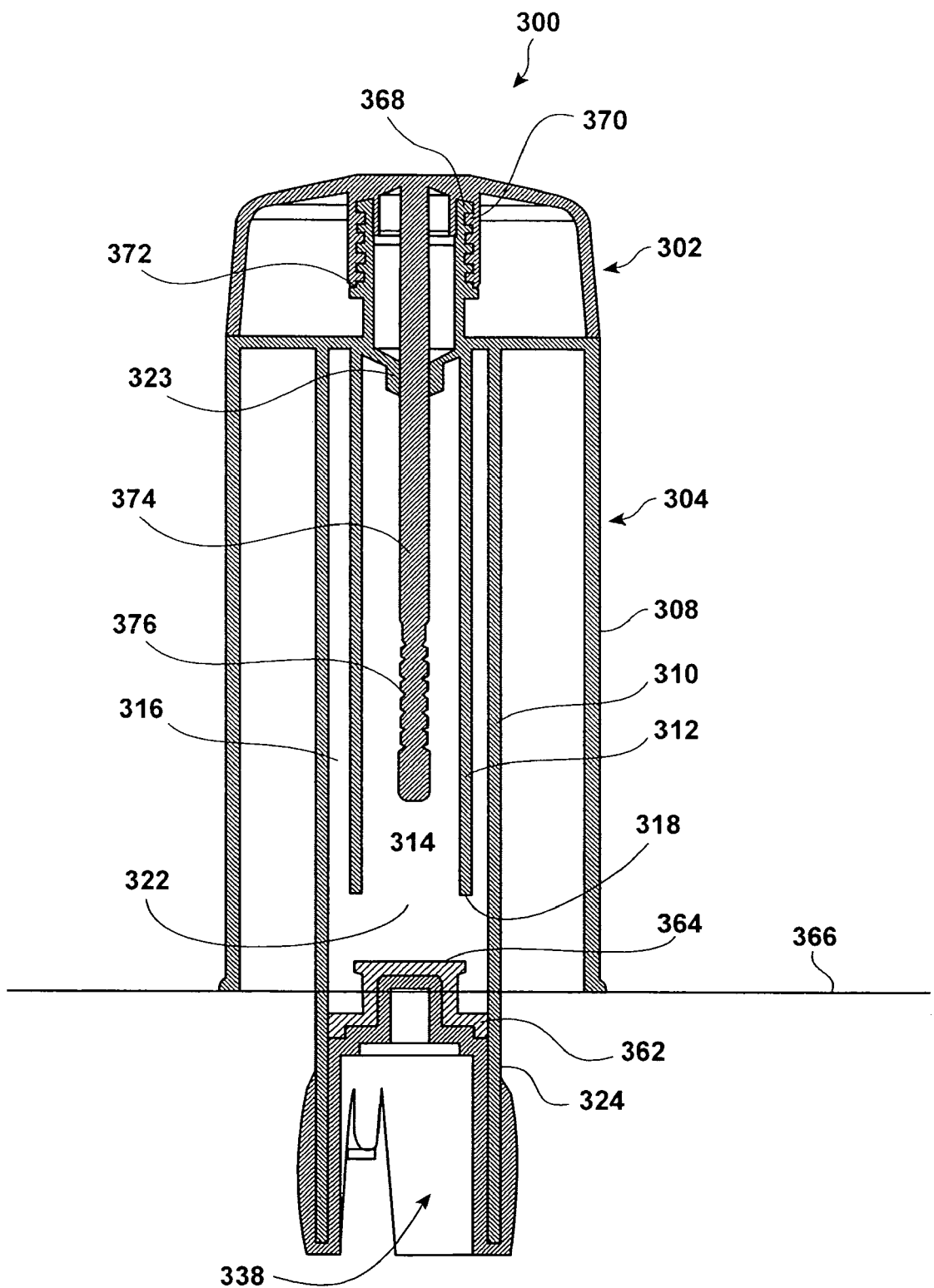
FIG. 3B is a cross-sectional view of the apparatus of FIG. 3A, shown without a portion of the base for clarity and in an open position.

Turning now to FIGS. 3A-3D, another embodiment of a sample handling apparatus comprising an assay test strip is shown. FIG. 3A is a cross sectional side view of an apparatus 300 in a closed position and FIG. 3B is a cross sectional side view of apparatus 300 in its activated position. Apparatus 300 comprises a removable top member 302, a test assembly 304, and a movable base 306.

Test assembly 304 comprises an exterior wall 308, a median wall 310, and an interior wall (or septum) 312. Interior wall 312 separates the interior chamber of the test assembly into a sample receiving chamber 314 and a test chamber 316. Interior wall 312 has a bottom portion 318 and a top portion 320. The bottom portion of the interior wall is open to form an opening 322, best seen in FIG. 3B. Top portion 320 of the interior wall is open to form an upper opening 323, through which sample, and/or the sampling wand (i.e., sampling member) 374, is introduced into the sample receiving chamber.

With continuing reference to FIG. 3B, apparatus 300 is shown in an activated position, and an outer portion of base 306 is excluded from the drawing for visual clarity. In this illustration, it is seen that median wall 310 extends from proximal to the interior wall 312 top portion 320 of the test assembly beyond the bottom portion 318 of the interior wall 312, and into base portion 306. By extending into the base portion, the median wall provides a surface 324 upon the base portion can be rotated by a user, for example in the direction of arrow 326 seen in FIG. 3A, as described more fully below.

Figure 3C:
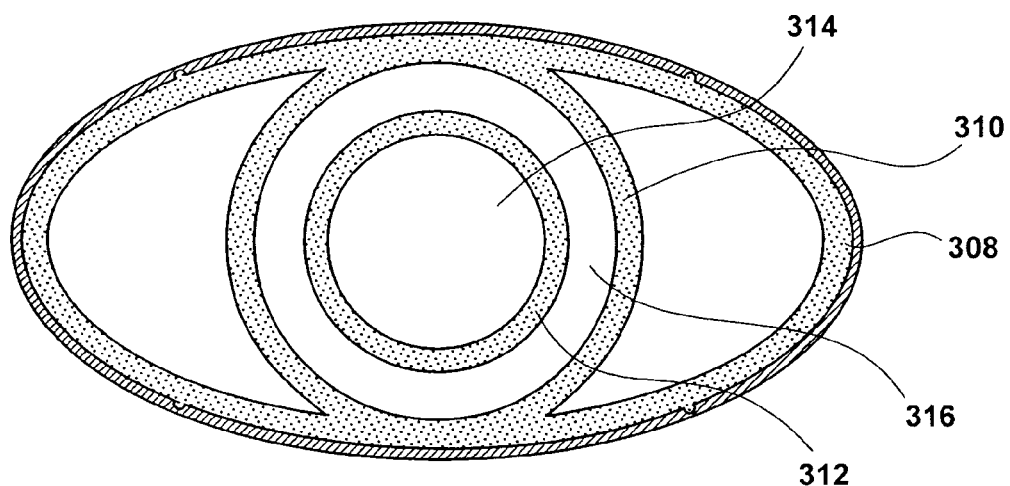
FIG. 3C is a cross-sectional view through line A-A in the apparatus of FIG. 3A

A cross-sectional view of assembly housing 304 is shown in FIG. 3C, which is a cross-sectional view along line A-A in FIG. 3A. Exterior wall 308, median wall 310, and interior wall 312 are seen. Median wall 310 and interior wall 312 together define test chamber 316. Interior wall 312 defines the sample receiving chamber 314. As will be described below, a later flow immunoassay test strip is positioned in test chamber 316. It is also contemplated that a sachet, strip, or packet comprising a desiccant can be positioned in the test chamber, if desired.

Figure 3D:
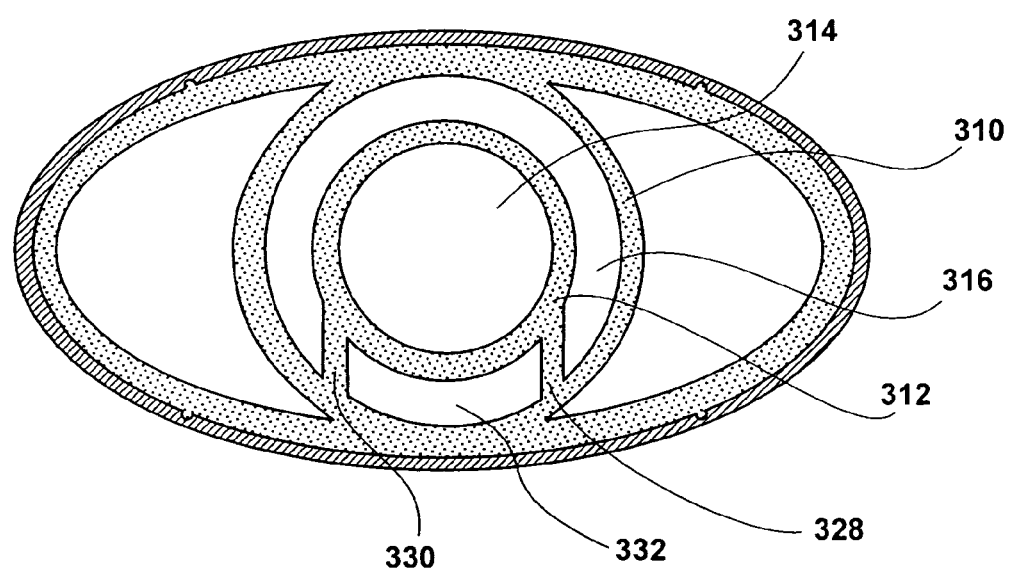
FIG. 3D is a cross-sectional view of an alternative embodiment of the apparatus of FIG. 3A.

It is also contemplated that additional chambers in the assembly housing can be created, for example by fabricating two or more lateral wall members, such as members 328, 330 seen in FIG. 3D, that connect interior wall 312 and median wall 310. Lateral wall members 328, 330 and the interior and median walls, 312 and 310, respectively, define a sub-chamber 332. The sub-chamber can be in fluid communication with one or both of the sample receiving chamber 314 and the test chamber 316. By way of example, the lateral walls 328 and 330 may terminate at the bottom portion 318 of the interior wall 312 such that the sub-chamber 332 is in fluid communication with the sample receiving chamber 314 and the test chamber 316 via opening 322. In some embodiments, the sub-chamber 332 is used to house the lateral flow assay test strip and the test chamber 316 is used to house a desiccant material. Alternatively, each of the test chamber 316 and sub-chamber 332 can house an assay test strip or the sub-chamber can house a desiccant material, a fluid to maintain a pre-selected humidity, and/or a test reagent and the test chamber 316 can house an assay test strip. It will be appreciated that more than one assay test strip may be placed within a single chamber. It will be further appreciated that additional lateral wall members can be fabricated to create additional sub-chambers in the device and that such a plurality of sub-chambers may be employed within the device to, for example, provide separate storage of reagents, particularly liquid reagents, until activation of the device by a user.

The test chamber or any of the sub-chambers, and in particular any sub-chamber intended for housing an assay test strip, can be fabricated to include internal ribs, guides, pins, or other structures to locate and/or hold such lateral flow assay test strip or other membrane, filter, or similar assay component, in place. Similarly, where a chamber or sub-chamber is used to house a desiccant, the desiccant may be deposited on or within a strip or filter, which is held in place by internal ribs, guides, pins, or other structures positioned within the chamber, such as extending from the inner wall of the chamber.

With reference again to FIG. 3A, in the particular embodiment illustrated, exterior wall 308 and median wall 310 define a space 334. It will be appreciated that the housing assembly can be fabricated to divide space 334 into one or more discrete chambers, for example, for use in housing an additional assay test strip, or for containing liquid to maintain a pre-selected humidity, for containing liquid reagents, for use as a desiccant chamber, for use in containing instructions, advertising materials, decorative materials, or for any other use. It will be further appreciated that space 334 can be eliminated from the device by, for example, manufacturing the device such that exterior wall 308 occupies the space adjacent to median wall 310.

Figure 3E:
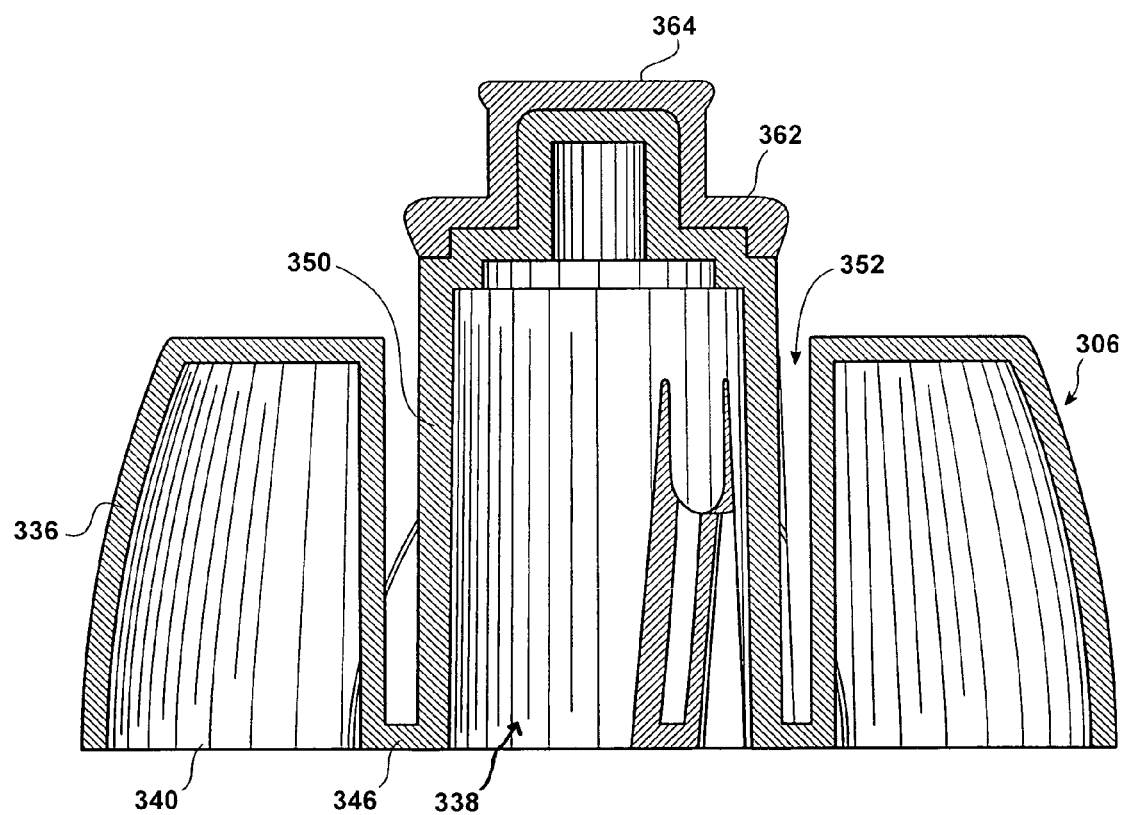
FIGS. 3E-3G are views of the base portion of the apparatus, where
Figure 3F:
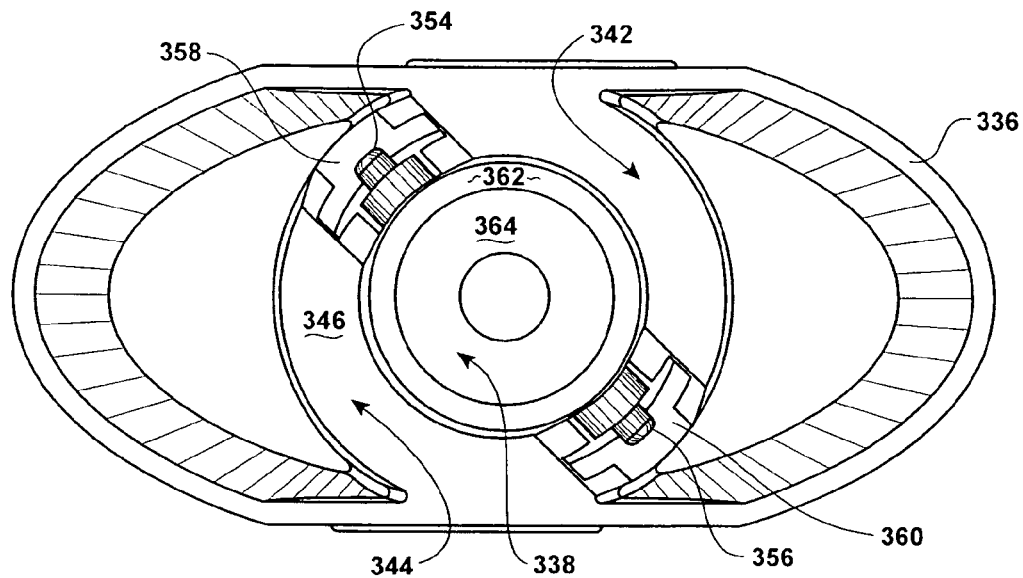
Figure 3G:
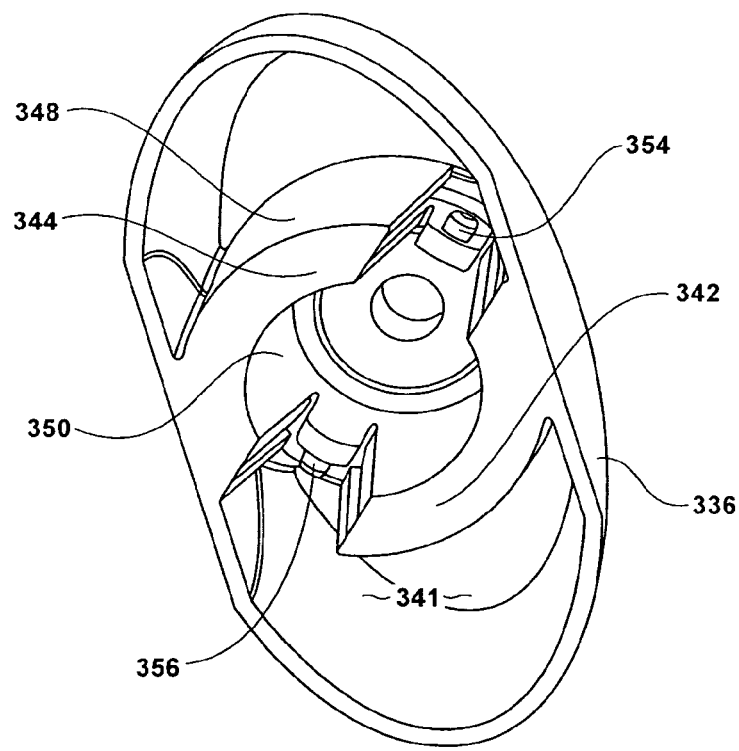

Base 306 is illustrated in more detail in FIGS. 3E-3G. FIG. 3E is a cross-sectional side view of the base portion, and FIGS. 3F-3G are plan and perspective bottom views, respectively, of the base portion. Base 306 is comprised of an outer wall 336, that, in this embodiment, is integral with a valve member 338 disposed within a chamber 341 formed by the outer wall. As seen best in FIG. 3G, outer wall 336 is integral with extension members 342, 344, that extend into chamber 341 formed by the outer wall of the base portion. Extension members 342, 344 are curved, and are comprised of a floor, such as floor 346 of extension member 344, and outer side wall 348 and an inner side wall 350. Outer and inner side walls 348, 350 define a gap 352 into which median wall 310 slidably fits, to connect assembly housing 304 with base 306. To secure assembly housing 304 into the base portion, one or more guide members, such as guide members 354, 356, are positioned in spaces 358, 360 between extension members 342, 344. The guide members are insertable into a groove in median wall 310, not seen in the embodiment of FIGS. 3A-3G, but shown in the embodiment of FIGS. 4A-4C, discussed below. As can be appreciated, the guide members serve to limit movement of the base portion to the length of the groove in which the members travel upon rotation of the base portion by a user.

Valve member 338 is dimensioned for contact with opening 322, to provide a means for control of fluid flow from the sample receiving chamber via opening 322 to the test chamber and/or any sub-chambers. In the embodiment shown in FIG. 3E, valve member 338 is defined in its lower region by the inner side walls of the extension members, such as inner side wall 350 of extension member 344. Valve member in its upper region, that is the region that contacts the test assembly, is comprised of an outer seal 362 and an inner seal 364. When the valve member is in its closed position, as depicted in FIG. 3A, outer seal 362 is in contact with median wall 310, and inner seal 364 is in contact with inner wall 312. When the valve member is in its activated position, as depicted in FIG. 3B, outer seal 362 is in contact with median wall 310, and inner seal 364 is no longer in contact with inner wall 312, such that opening 322 is not blocked or plugged by the inner seal of the valve member, permitting fluid communication between the sample receiving chamber and the test chamber. As mentioned above, valve member 338 is moved between its open (or activated) and closed positions by turning, rotating or twisting base 306 about a horizontal axis 366 (see FIGS. 3A and 3B) in the clockwise and counter clockwise directions. The valve is preferably designed such that particulate matter, which may be present particularly in solid or semi-solid biological samples, does not clog or prevent flow of liquid from the sample receiving chamber to the test chamber.

When valve member 338 is in its closed position as depicted in FIG. 3A, sample receiving chamber 314 is isolated from test chamber 316, allowing a sample, a buffer or reagent, or a sample and reagent/buffer, to be stored in the sample receiving chamber. When valve member 338 is in a partial or fully activated position, as depicted in FIG. 3B, the contents of the sample receiving chamber can flow from the sample receiving chamber to the test chamber, and/or to any sub-chambers. The valve member may provide essentially "on" or "off" control of flow, or may provide a variable rate of flow depending on the valve position (e.g., ¼ open, ½ open, full open, etc.). The valve may also meter the amount of liquid that is allowed to flow from the sample receiving chamber to the test chamber. In this manner, the valve can be used to modulate both rate and quantity of fluid flow from the sample receiving chamber to the test chamber, where such control is desired.

As can be appreciated, the valve disposed within the base can be any type of valve suitable for modulating fluid flow, including but not limited to rotary, gate, ball, needle, butterfly, pinch, bellows, piston, slide, plug, diverter, stopcock, and actuator valves.

It will be appreciated that the valve member may include a seal, such as an o-ring, overmold, or gasket, disposed on one or both of outer seal 362 and inner seal 364. For example, a valve overmold may be placed over the valve member face that engages the test assembly, to form a robust seal against the opening 322. Valve overmolds may be made of suitable resilient elastomeric materials, including but not limited to nylon; vinyl, polyethylene, polypropylene, polyester, epoxy, polyolefins, silicone, fluoropolymers, and polyurethanes; naturally occurring materials such as wax, cork, asbestos, rubber, chicle; or metals such as copper, brass, steel, lead, tin and gold and their alloys. The valve member and its components can be manufactured using various materials, including metal, silicon, glass, ceramic, plastic, synthetic and natural polymers, or any combination thereof. For example, the valve member can be manufactured from a polypropylene composition using an appropriate manufacturing method such as pressure injection molding or machining. The method of production largely depends on the design of the valves and intended volume of the sample receiving chamber. Other methods of manufacturing include but are not limited to milling, casting, blowing, and spinning. It will be appreciated that valve member and valve overmold materials are chosen to be compatible not only with their intended function but with the sample, reagents and/or other materials with which such components will come in contact.

The inner seal 364 can take any number of different configurations. For example, the seal can have a substantially oval (including round) cross section when viewed on end. Alternatively, the seal can be rectangular with a substantially square or rectangular cross section when viewed on end. The inner seal 364 may have a tapered surface to improve the flow rate of the sample from the sample receiving chamber to the test chamber, once the valve member has been activated (i.e., opened). In a particular embodiment, the inner seal is substantially cylindrical.

In some embodiments, the valve member is designed for exposure to nominal atmospheric pressure, with minimal pressure differential between the sample receiving chamber and the test chamber. In other embodiments, particularly where the test apparatus is intended to be transported via aircraft, the valve is designed to tolerate a greater differential pressure between the sample receiving chamber and the test chamber. Similarly, where the apparatus is part of an automated fluidic or microfluidic rapid test apparatus, the valve member is designed to withstand a considerable pressure differential between the sample receiving chamber and the test chamber. Contemplated pressure differentials are from about one third the standard air pressure at sea level (i.e., 0.333 atmospheres) to at least about 2, 3, 4, or even 5 atmospheres pressure differential. Design of the valve member to tolerate a selected pressure differential is achieved through selection of the valve material, the shapes of the inner and outer seals, and/or the presence or absence of o-rings, gaskets, or overmolds on the inner and outer seals.

With reference again to FIG. 3A, optional top member 302 is dimensioned to engage with the test assembly. In one embodiment, the top member comprises an internal thread 368 to engage a thread 370 in a neck region 372 of test assembly 304. Top member can also comprise a sampling wand (or member) 374 integrally formed with the top member, or removably insertable into the top member. The sampling wand as depicted in FIGS. 3A-3B has grooves or serrations 376 in all or a portion of the sampling wand, for increased retention of a biological sample and increased surface area on which to retain a solid, semi-solid, or fluid biological sample. Sampling wand, when present, is insertable into opening 323 in the upper region of the test assembly. Opening 323 provides an access port for introduction of a biological sample into the sample receiving chamber, the sample placed on the sampling wand prior to its insertion through opening 323. It will be appreciated that the sampling wand is optional, and even if present need not be utilized, as a user may simply introduce a biological sample directly through opening 323 into the sample receiving chamber.

Figures 4A, 4B, 4C:
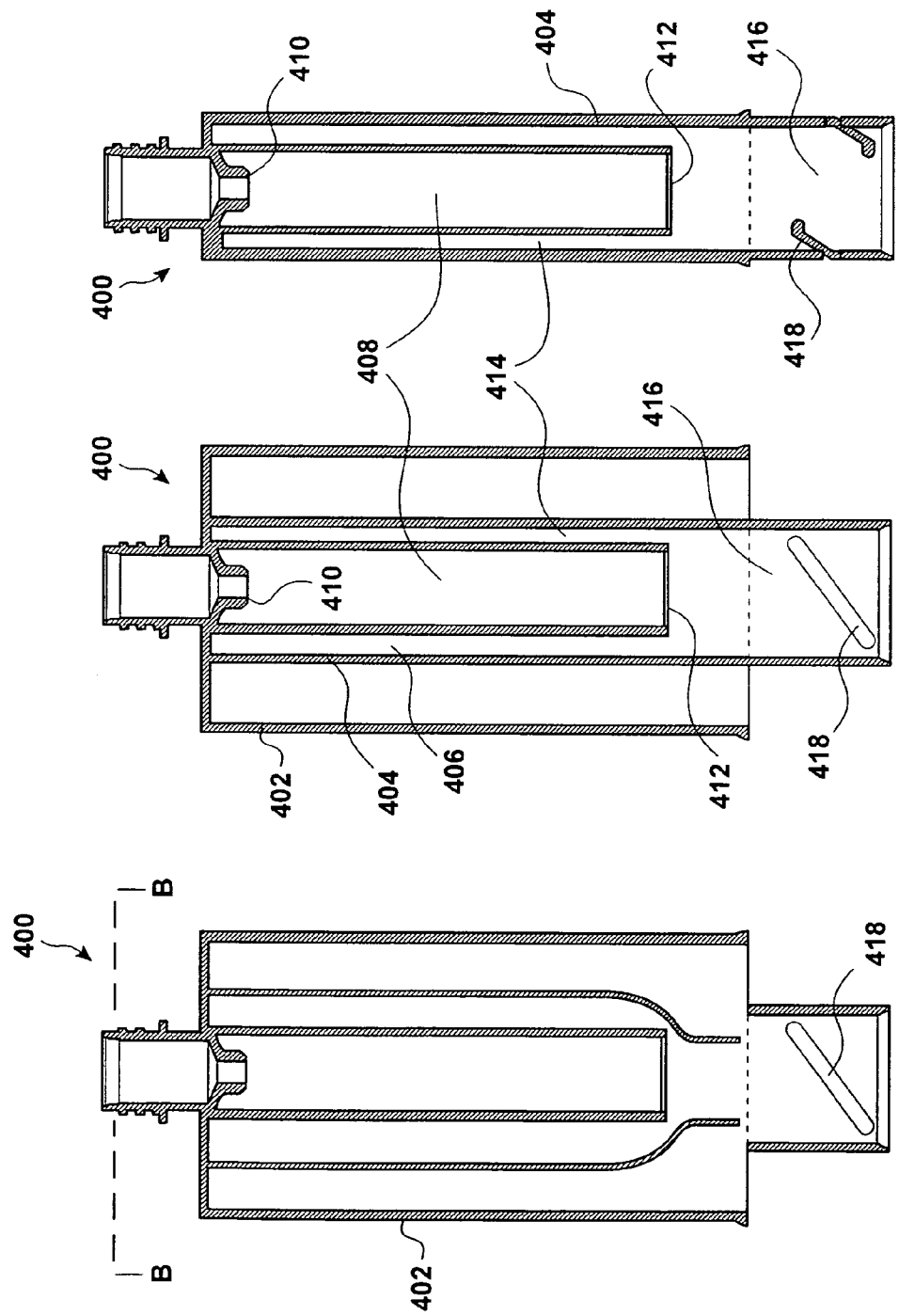
FIGS. 4A-4C are cross-sectional views of another embodiment of an apparatus for use in receiving a biological sample and detection of an analyte of interest.

As noted above, the movement of the valve member in the base of the test assembly can be controlled, in one embodiment, by one or more guide members disposed in the base that engage with, for example, a groove in the test assembly. This embodiment is illustrated in FIGS. 4A-4C, where a test assembly 400 is shown in side view (FIG. 4A), and in FIGS. 4B-4C in cross-sectional views taken along line B-B, where the cross-sectional view of the test assembly of FIG. 4C is rotated about 90° relative to the view in FIGS. 4A-4B. Test assembly 400 is comprised of an external wall 402, a median wall 404, and an inner wall 406. Inner wall 406 defines a sample receiving chamber 408 that is open at its upper end to provide opening 410 and at its lower end to provide opening 412. The median wall and the inner wall together define a test chamber 414 that can be in fluid communication with the sample receiving chamber. A lower region 416 of median wall 404 extends past external wall 402, and is dimensioned for insertion into a bases member (not seen in FIGS. 4A-4C). Median wall 404 has one or more grooves, such as groove 418, in which one or more guide members within a base can be inserted. It will be appreciated that the length and angle of the one or more grooves in the median wall determine the total possible movement of the base, and therefore of the valve member. The base is moveable a distance corresponding to the length of the groove, where guide pins in the base provide a full stop position of the base, that corresponds to a fully activated or open position of the valve within the base. The guide members in the base and inserted into the groove prevent the base from turning beyond a preselected amount, and prevent the base from disengaging from the test assembly which would cause a loss of sample from the sample receiving chamber. In this embodiment, the length of the grooves 418 determines the amount of rotation of the base, which is typically about ¼ or ½-turn. Use of a ¼-turn base offers the advantage that the open (i.e., activated) and closed positions are visually distinct, particularly when the test assembly has an oval oblong outer dimension. Any amount of rotation can be engineered into the mechanism without departing from the description. In addition, any number of grooves and/or detents can be provided between the test assembly and the base to prevent accidental turning of the base, e.g., to provide a positive indication of the open (i.e., activated) and closed positions. Alternatively or additionally, a label or tape may be placed on the apparatus to prevent the base from turning on the test assembly until the label or tape is removed.

In operation of the device of FIGS. 3A-3E, a solid, semi-solid, or liquid biological sample is introduced into the sample receiving chamber when the valve member is closed placing the device in a "deactivated" state. The sample may be introduced using the sampling wand attached to the optional cap member, or by otherwise introducing the sample into the sample receiving chamber, for example, using a sterile or sanitary applicator stick, cotton swab, eye dropper, or the like. Materials that have contacted biological samples, or that include biological samples, may also be introduced into the sample receiving chamber. For example a piece of tissue, gauze, cotton, filter material, or other material that has contacted blood, sputum, mucous, feces, semen, or other biological sample may be placed directly in the sample receiving chamber.

The cap if present can then closed, e.g., by threading the cap into or onto the test assembly. Following sample preparation by mixing or shaking and waiting any time period required by the particular assays(s), the base is rotated, causing the guide members to slide in the grooves of the median wall, moving the valve member away from the sample receiving chamber, and activating the apparatus. Activation of the apparatus involves movement of the valve member to an open position, to open the opening between the sample receiving chamber and the test chamber, allowing sample to flow into the test chamber. Disposed in the test chamber is an immunoassay test strip, that wicks or absorbs sample solution. An assay result(s) can be read on the assay test strip, which is visible through one or both of the exterior wall and/or the median wall. Assay test strips are described below with respect to FIG. 6.

Another embodiment of an apparatus is illustrated in FIGS. 5A-5D. Apparatus 500 is comprised of a cap member 502 seen in FIG. 5A but absent in FIGS. 5B-5C, a test assembly 504, and a base 506 seen in FIG. 5A but absent in FIGS. 5B-5C for visual clarity. Test assembly 504 is similar to that described above with respect to FIGS. 4A-4B, and has a median wall 508 that extends the length of the test assembly and provides a surface 510 for engaging base 506. Median wall 508 has one or more grooves, such as groove 510 in FIGS. 5A-5B and groove 512 in FIG. 5C. Median wall can additionally include a separate cut out, such as cut out 514 in FIG. 5B, or can include a side arm, such as side arm 516 of groove 512 in FIG. 5C. The cut out and the side arm function to define a flexible wall portion, such as flexible wall portions 518, 520 in FIGS. 5B-5C respectively. The flexible wall portion eases insertion of a guide member into the groove, and movement of the guide member within the groove. An exemplary guide member is shown in base 506, shown in cut-away view in FIG. 5D. Visible in the cut-away region is a guide member 522 dimensioned for insertion into a groove in a median wall, such as groove 510 of FIG. 5C.

Figure 5A:
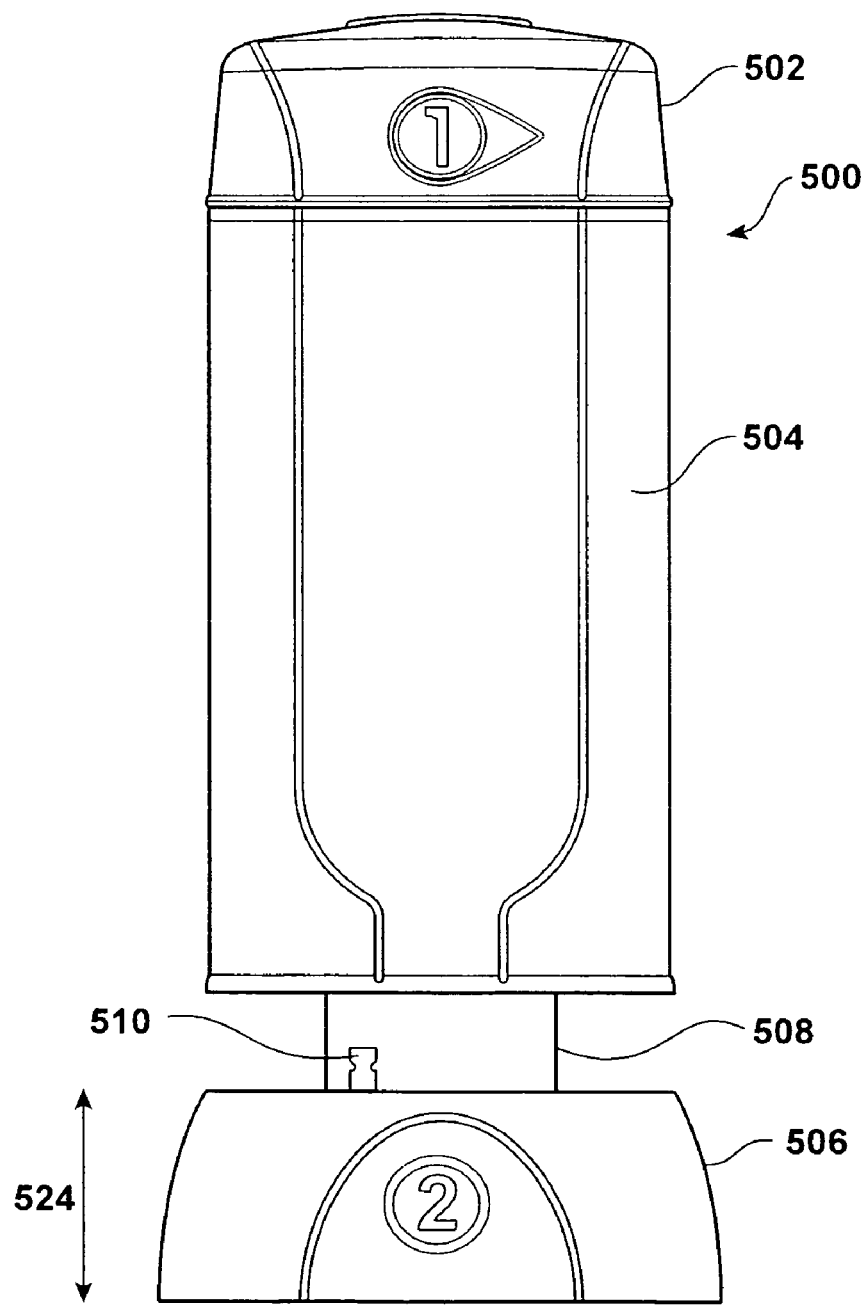
FIGS. 5A-5D are side views of yet another embodiment of an apparatus for use in receiving a biological sample and detecting an analyte of interest.

In the embodiment of FIG. 5A-5D, base 506 is moveable by a user in an upward and downward motion, as illustrated by arrow 524 in FIG. 5A. The distance of travel of base 506 is determined by the length of the groove in the median wall. The shape of the grove determines whether the base can be placed in an open (or activated) and "locked" position. For example, as seen in groove 510 of FIG. 5B, narrowing regions 526, 528 require slightly more pressure to move a guide pin past the narrowing region. A guide member, when positioned between a narrowing region and a terminal end of a groove is "locked" in place, securing the valve member in an open (i.e., activated) or in a closed position.

As mentioned above, the apparatus described herein comprises one or more immunoassay test strips placed in the test chamber of the apparatus and/or in one or more sub-chambers. Assay strips for use with the apparatus can be of any format known in the art; however, lateral flow assay strips are preferred. Assay strips may be of any shape or size but are typically rectangular, and an apparatus may include one or more assay strips. The one or more assay strips can be placed separately within the test chamber or arrayed on a common support and placed together within the test chamber. As noted above, the test chamber may be divided into sub-test chambers, which are ideal for containing one or more assay strips. In such cases, one or more sub-test chambers may be referred to as assay strip chambers. An assay strip chamber may contain a single assays strip, an array of assay strips, or a plurality of assay strips; however, the one or more assay strips should preferably be positioned such that the assay results are visible from outside the apparatus, without the need to remove the strip(s).

Figure 6:
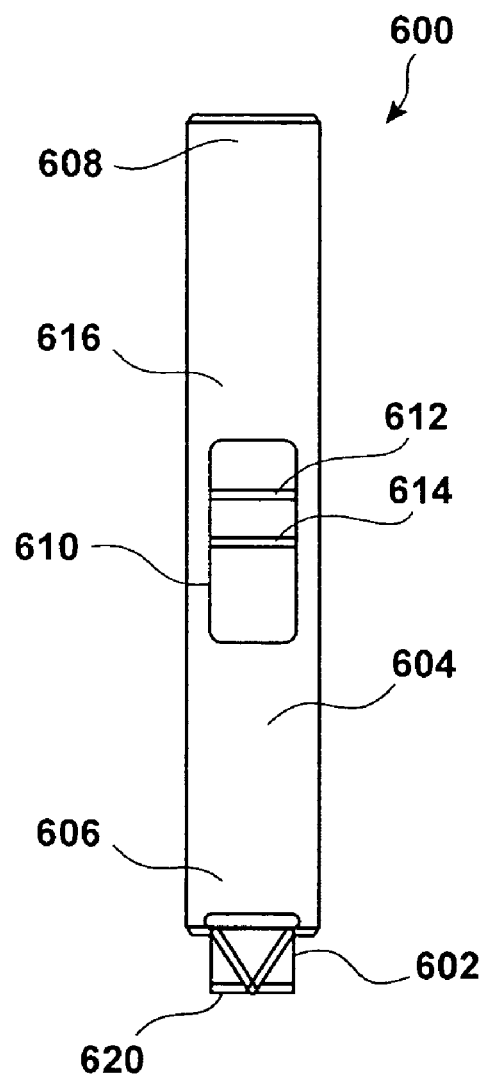
FIG. 6 is a top view of an immunoassay test strip contained within a strip holder sleeve.

The immunoassay test strip may be placed directly in the test chamber or may be secured in an immunoassay strip holder sleeve prior to placement in the test chamber. FIG. 6 illustrates the latter option, where an immunoassay test strip assembly 600 is comprised of an immunoassay test strip 602 secured within a strip holder sleeve 604. Strip holder sleeve 604 has an opening on at least a lower end 606 or an upper end 608 of the sleeve, and the opening or openings are dimensioned for insertion of the immunoassay test strip. The strip holder sleeve comprises an open region 610 positioned on the sleeve such that when the immunoassay test strip is positioned within the sleeve, a test line 612 and/or a control line 614 on the test strip are visible. The strip holder sleeve preferably supports the immunoassay test strip in a substantially flat condition, and minimizes oversaturation of the strip by a sample solution. The strip holder sleeve may have ribs, grooves, serrations, or other structures along its outer surface 616 to ease handling the sleeve. When inserted into a test chamber of an apparatus described herein, the strip holder and test strip are preferably positioned such that the sample solution contacts at least lower end 606 of the assembly, and in a preferred embodiment, only a bottom region, e.g, the lower ¼ or ⅓, of the test strip.

In one embodiment, the strip holder sleeve comprises a tip, such as triangular point 620 seen in the strip holder sleeve of FIG. 6. In this optional embodiment, the strip holder sleeve terminates in a point, which serves to reduce and/or minimize formation of bubbles when the sample solution enters the test chamber and contacts the strip holder sleeve. The triangular portion 620 aids in flow of the sample into the assay strip 602 and disrupts bubbles or reduces undesirable surface tension effects. The shape and size of the triangular portion are not critical, so long as it promotes the flow of sample into the bottom portion of the test strip and/or disrupts bubble formation.

As previously described, assay test results may be viewed through the exterior wall of the test assembly, which is preferably transparent or includes a transparent section or window. However, to ensure privacy in the test results, the portion of the test apparatus through which the test result is visible can be covered to obscure the immunoassay test strip. In some embodiments, a removable opaque label or tape may be used. The label or tape may be provided on the apparatus when supplied to a user, or may be applied by the user, and is removed by the clinician or laboratory personnel for viewing the test result.

It is desirable, but not required, for there to be one or more labels or writing surfaces on the exterior wall of the test assembly on which to print, write or display information, such as the subject's name and age, the nature of the biological sample, the date, the clinician's name, and/or the like. Furthermore, surfaces of the apparatus not in contact with fluid or not required to be transparent for viewing the assay results, such as the cap and base, can include writing or embossed information to assist the user. In one example, the cap and/or base are embossed with letters or numbers that correspond to letters or numbers in instructions provided for using the apparatus.

C. Materials for Manufacture of the Apparatus

Numerous materials can be used to manufacture the testing assembly, structures within the testing assembly (e.g., exterior wall, median wall, interior wall, and lateral walls, the strip holder sleeve), the base, and/or the cap. Exemplary materials include synthetic and natural polymers, metal, silicon, glass, ceramic, and combinations and mixtures thereof. In one embodiment, the walls of the test assembly and/or the strip holder sleeve are manufactured from a polypropylene composition using an appropriate manufacturing method such as pressure injection molding or machining. Other suitable polymers include polystyrene, polycarbonate, and other polymers commonly used in the medical apparatus and food industry. Preferred polymers do not interfere with the assay(s), such as by binding protein substances in the biological sample or leaching reactive substances into the assay. The apparatus may be manufactured as a single component or assembled from multiple components. Suitable methods of manufacturing include but are not limited to injection molding, casting, milling, micro-machining, blowing, and spinning.

In a preferred embodiment, thermoplastic injection molding is used to manufacture the test assembly, base, and/or other elements of the test apparatus described herein. Numerous available thermoplastics are biocompatible, transparent, strong, and have good molding characteristics. In a typical injection molding process, an injection cycle can be completed in less than one minute, and multiple molds or cavities allow for proportionally lower costs, a significant factor for production what may be a disposable system. Machining and/or drilling partially-molded thermoplastic materials can also be used to produce the test assembly, although the cost is likely to be greater than injection molding.

In some embodiments, the test assembly and base may be formed from a disposable, recyclable, reclaimed, or renewable material. Apparatus may be formed from a transparent material to allow for visual inspection of their contents, or include transparent panels, walls, or other sub-structures to allow for visual inspection of their contents. The use of transparent materials adjacent to the test strip allows a user to read the result on the test trip without first removing the test strip from the apparatus. Alternatively, an opaque material is used, requiring the test strip to be removed from the apparatus to read and analyze the assay result, which may be preferred when the assay result is of a personal nature.

In some embodiments, at least a portion of an outer surface adjacent the test strip may be configured to optically affect the contents of the receptacle when viewed from an exterior of the receptacle by a user and/or a doctor. For example, a portion of the apparatus may be configured to magnify a portion of the test strip to facilitate reading the result. Such magnifying structures may be substantially convex, as known in the art.

The physical dimensions of the rapid test apparatus can be varied to meet or exceed the volume of the biological sample and buffer to be contained within the sample receiving chamber. In particular, the sample receiving chamber size can be manufactured to accommodate sample volumes of between about 0.01 milliliter (mL) and about 1,000 mL. Sample receiving chamber volumes between about 0.1 mL and about 1,000 mL, between about 1.0 mL and about 999.9 mL, between about 10 mL and about 990 mL, between about 100 mL and about 900 mL, between about 200 mL and about 800 mL, between about 300 mL and about 700 mL, or between about 400 mL and about 600 mL are contemplated. Exemplary volumes include 0.5, 1, 2, 3, 4, 5, 6, 7, 8, 9, 10, 15, 20, 30, 40, 50, 60, 70, 80, 90, and 100 mL, although other volumes are acceptable.

Any of the embodiments may include one of more vents to prevent air pressure build-up in any chamber. Such vents should be air permeable but not fluid permeable. Exemplary materials for such vents are described, herein, and include polyethylene, polyvinylidine fluoride (e.g., as manufactured by the Porex, Corp.), and polytetrafluoroethylene, although other materials can be used.

D. Biological Samples and Method of Use

The present rapid test apparatus may be used to detect a variety of substances (or analytes) in solid, semi-solid, or liquid biological samples, including drugs of abuse, alcohol, therapeutic drugs, micro-organisms, infectious pathogens, bacteria, viruses, fungi, parasites, blood components, antibodies, hapto-hemoglobin complexes, enzymes, proteins, allergens, glucose, pH, creatinine, hormones, tumor markers, cardiac markers, pesticides, explosives, poisons, and environmental pollutants.

Biological samples for use with the rapid test apparatus include solid and semi-solid samples, such as feces, biopsy specimens, skin, nails, and hair, and liquid samples, such as urine, saliva, sputum, mucous, blood, plasma, serum, amniotic fluid, semen, vaginal secretions, tears, spinal fluid, washings, and other bodily fluids. Included among the sample are swab specimens from, e.g., the cervix, urethra, nostril, and throat. Any of such samples may be from a living, dead, or dying animal or a plant. Animals include mammals, such as humans. Other biological samples include samples of food products, animal feed, waste water, drinking water, sewage, soil, dust, and the like.

One application for the present rapid test apparatus is for detecting the presence of substances/analytes in a stool sample, which is typically solid or semi-solid, and not immediately useful in lateral flow assays. The present apparatus permits fecal sample collection, preparation, and testing, all using in a single apparatus with minimal handling.

In addition to identifying microorganisms, the rapid test apparatus may also be used to type pathogens, such as viruses, bacteria, fungi, or parasites. In one example, the apparatus is used to type flu virus as described in U.S. Pat. No. 5,415,994. Additional exemplary uses for the rapid test apparatus include but are not limited to detecting trichomonal and other hydrolases, as described in e.g., U.S. Pat. Nos. 7,291,481 and 7,041,469; chlamydia, as described in e.g., U.S. Pat. No. 5,773,234; chorionic gonadotropin, as described in, e.g., U.S. Pat. No. 4,496,654; creatinine, as described in e.g., U.S. Pat. No. 5,804,452; *Helicobacter pylori*, as described in e.g., U.S. Pat. No. 5,846,751; bacterial antigens, as described in e.g., U.S. Pat. No. 5,536,646; fertility and pregnancy, as described in e.g., U.S. Pat. Nos. 5,118,630 and 5,786,220; and sperm motility, as described in, e.g., U.S. Pat. No. 5,434,057. All of these patent are incorporated by reference herein.

Various features described for enhancing lateral flow assay may be adapted to the rapid test apparatus, such as those described in U.S. Pat. Nos. 4,943,522, 4,818,677, 5,268,146, 5,223,220, 5,763,262, 6,924,153, 5,766,961, 5,770,460, 6,855,561, 6,451,607, 6,306,642, 7,179,657, 7,255,832, 7,226,793, 7,144,742, 6,706,539, 6,656,744, 5,783,401, 5,741,662, 5,686,315, 5,541,069, 5,521,102, 5,415,994, 5,225,328, and 5,221,616, and U.S. Pat. Pub. Nos. 2007/0243630, 2007/0111323, 2007/0281370, 2006/0078986, 2005/0227371, and 2004/0152207.

E. Reagents for Use in Test Apparatus

Various reagents can be used to prepare the sample buffer, assay strip, and desiccant for use in the rapid test apparatus.

For example, the sample buffer may include water, salts, solvents, surfactants, buffering agents, proteases, protease inhibitors, nucleases, nuclease inhibitors, lipases, amylases, dyes and coloring agents, glycerol, and other reagents, depending on the particular substances being detected and the type of assay being performed. Where the biological sample is solid or semi-solid, the sample buffer should be in liquid form. Where the biological sample is a liquid, the sample buffer may be in liquid or dry form.

Assay reagents that produce a detectable signal in the presence of at least one substance or analyte and may be in dry or liquid form. Dry assay reagents (including air-dried or lyophilized reagents), generally have a longer shelf life than liquid reagents, and may be preferred in some embodiments. Assay reagents may include a buffer component (as above) and one or more reagents for detecting a particular substance or analyte. In some embodiments, assay strips include one or more assay reagents that react specifically with a substance/analyte in the biological sample to produce a product, and one or more assay reagents that produce a detectable signal in the presence of that product.

In some embodiments, the rapid test apparatus is used to perform an immunoassay, and one or more of the assay reagents is an antibody, or fragment or derivative, thereof. Antibody reagents are generally stable for prolonged periods of time in liquid fonn and in dry form and are available for detecting a wide variety of clinically or environmentally relevant substances present in biological samples, and such antibodies need not be described in detail. In particular embodiments, antibodies may be used in combination with one or more additional reagents to produce a detectable signal upon binding of the antibody to a target analyte. By way of example, a label reagent comprising an antibody, capable of binding to the analyte of interest, and conjugated to a detectable label, such as a colored particulate label for example, a colored latex bead or metal sol, may be releasably applied to a label pad portion of and immunoassay test strip. A second, capture reagent, comprising a second antibody, capable of binding the analyte/label reagent compound, is immobilized in a test region of the immunoassay test strip such that analyte/label reagent present in the migrating sample is captured. The accumulation of label at the test line then provides a visual signal of the presence of analyte in the sample. Alternatively, labels may be selected that provide a fluorescent or radioactive or magnetic or similar non-visual indication of the presence of analyte in the sample. In such alternative cases, a reader or similar detection means must be employed to detect the presence of signal, if any, at the test line.

In addition to antibodies, other assays reagents include substrates for enzymes present in the sample that produce a colorimetric product, enzymes that catalyze conversion of an analyte in the sample to a detectable product, polynucleotides (e.g., probes) that hybridize to particular nucleic acids in the sample, and the like.

Where the rapid test apparatus includes a desiccant, it is preferred that the desiccant is integrated into the apparatus in the form of a film membrane molded piece, for example, a polyethylene film having desiccant dispersed therein. An example of a desiccant in the form of a film or tape is described in U.S. Pat. Nos. 7,005,459 and 6,613,405, which are incorporated by reference herein. In this form, the desiccant provides a stable, non-reactive, non-corrosive material that does not leave particulates capable of interfering with performance of the apparatus, as can occur when a desiccant is in a loose form or in a sachet. The desiccant need not be sequestered from other parts of the apparatus, such as by placement away from certain portions of the apparatus, by use of a protective coating over the desiccant, or by packaging of the desiccant within other materials to form a sachet or film that is removed prior to use of the apparatus. That is, the desiccant material may be in contact with the sample, need not be removed prior to use, and does not interfere with performance of the apparatus.

Examples of desiccants include, but are not limited to, molecular sieve, alumina, bauxite, anhydrous calcium sulfate, water-absorbing clays, silica gel, zeolite and any of the other moisture-absorbing materials known to the art. Other exemplary desiccants are described in detail in U.S. Pat. Nos. 5,911,937, 6,214,255, 7,005,459, 6,613,405 and 6,130,263, which are incorporated by reference herein.

A desiccant material may be secured to one or more regions of a smaller chamber 450, 416 using an adhesive. Examples of adhesives include, but are not limited to paste, putty, rubber cement, mucilage, birdlime, sealant, epoxy, and stickum. Exemplary adhesives are silicone, epoxy, or cyanoacrylate-based, although other adhesives can be used. In other embodiments, the desiccant is integrated into the apparatus by lamination of a desiccant or desiccant-containing material to one or more regions of the test chamber 450, 416 (or sub-test chamber). In another embodiment, the desiccant is integrated into the apparatus by a mechanical means. Examples of mechanical means include, but are not limited to staples, rivets, pins, straps, leashes, ribs, notches, etc.

The sample buffer may further include one or more reagents to disinfect a biological sample or deactivate infectious agents within a biological sample, including but not limited to alcohols, chlorine compounds, phenolic compounds, quaternary ammonium compounds, iodophors, or antibodies, so long as they do not interfere with the assay.

F. Kits

Kits for detecting substances present in solid, semi-solid, or liquid biological samples are also provided. The kits may include instructions for obtaining biological samples and contacting them with sample buffer, for mixing the samples with sample buffer, placing labels on the apparatus and recording relevant test data; for shipping the apparatus, and the like. The kits may include instructions for reading and interpreting the results of an assay. The kits may further comprise reference samples that may be used to compare test results with the specimen samples.

The entirety of each patent, patent application, publication and document referenced herein is hereby incorporated by reference.

EXAMPLES

The following examples describe a few of the many assays that can be performed using the test apparatus, and demonstrate the stability of test strips in the device.

Example 1

Apparatus for Fecal Occult Blood Test

An immunochemical fecal occult blood test or iFOBT is an immunoassay based test method for detection of human blood in stool specimens. The presence of hemoglobin in feces can be indicative of gastrointestinal tract conditions associated with bleeding such as, for example, colorectal carcinoma, colon polyps, Crohn's disease, and ulcerative colitis.

An apparatus as illustrated in FIGS. 3A-3G or 5A-B, and containing appropriate assay buffer in the sample-receiving chamber, is provided to a user. The user collects his/her feces, for example on a flushable, paper sheet secured across the seat of a toilet. The user removes the cap and the sampling wand from the rapid test apparatus, and inserts the sampling wand into the fecal sample, for example multiple times in order to obtain sample from different portions of the sample. The sampling wand (member)/cap portion is then reinserted into the test apparatus, which causes insertion of the sampling wand into the buffer within the sample-receiving chamber of apparatus. The cap is tightened securely and the apparatus is gently shaken to solubilize the fecal sample to obtain a liquid suspension of buffer and the biological sample. The test apparatus is then transported, for example, via first class mail, to a laboratory.

Figure 5B:
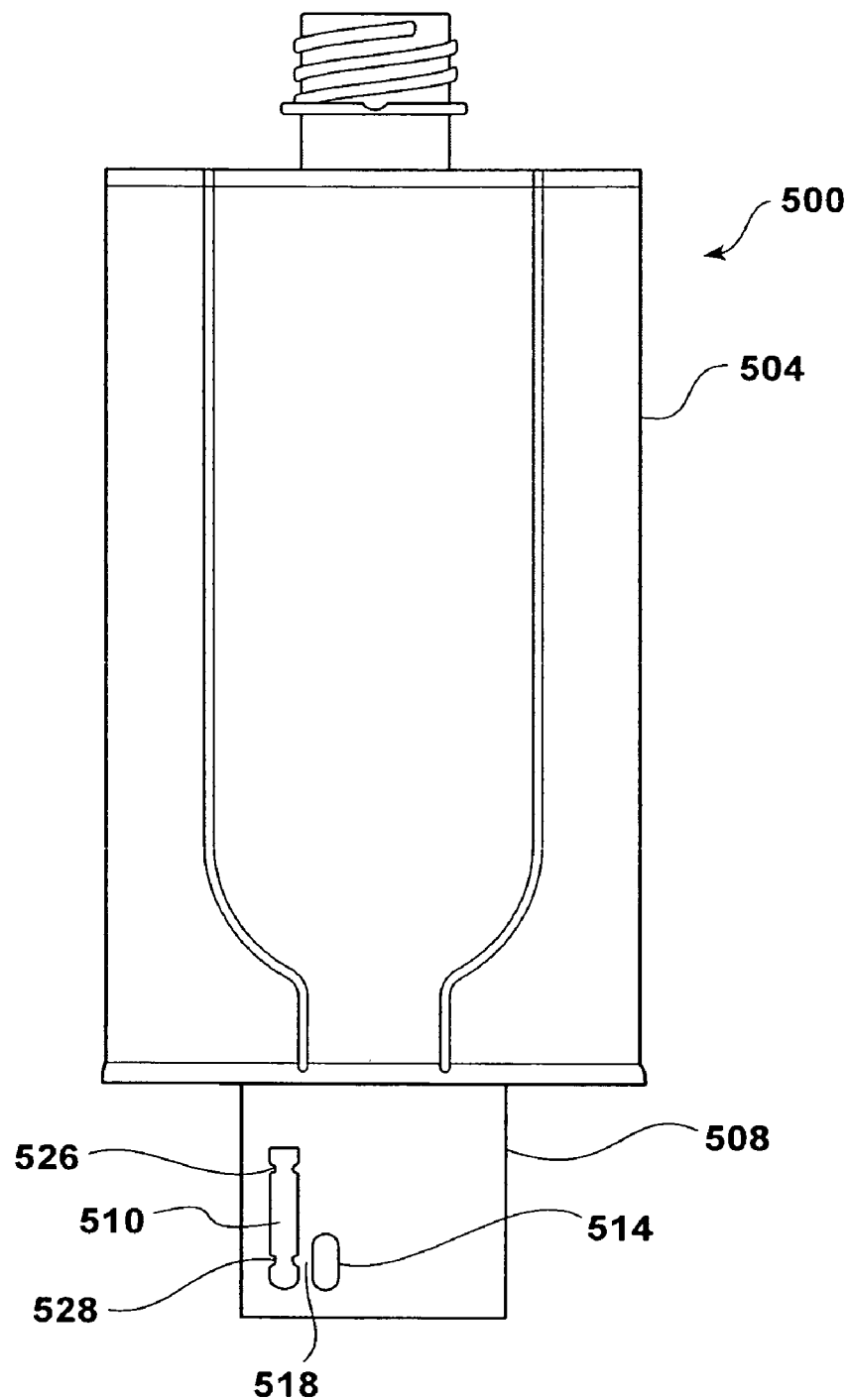
Figure 5C:
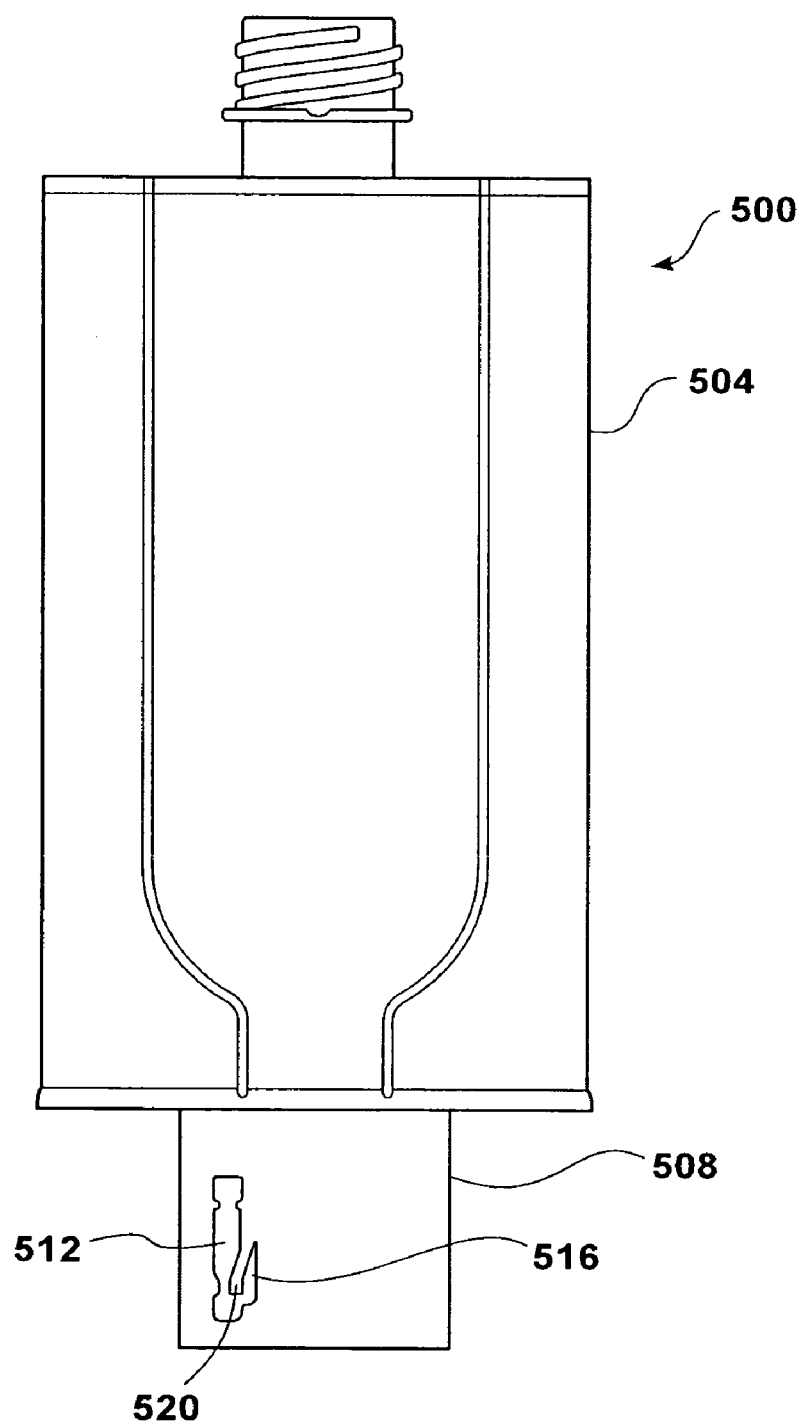
Figure 5D:
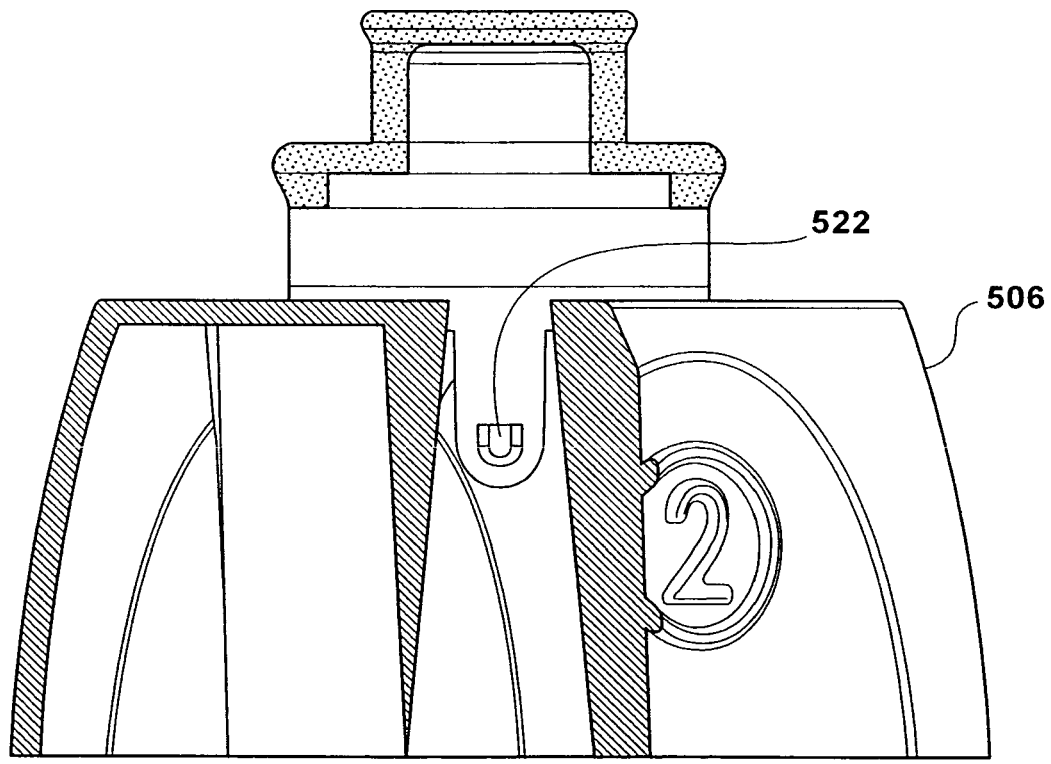

Upon receipt at the laboratory, a technician holds the apparatus upright and, in the case of an apparatus as illustrated in FIGS. 3A-G, rotates the base to move the valve from a closed position to an open position, causing the buffer/sample suspension to flow from the sample receiving chamber to the test chamber, contacting the immunoassay strip. In the case of an apparatus as illustrated in FIGS. 5A-B, the technician holds the apparatus upright and pulls the base down to move the valve from a closed position to an open (or activated) position, to cause the buffer/sample suspension to flow from the sample receiving chamber to the test chamber. In each case, after several minutes, the test and control lines on the immunoassay test strip are viewed through the transparent wall of the test assembly, to determine a result. In this particular assay, a negative test is indicated when one rose-pink color band appears in the control zone, meaning that the fecal sample does not contain a detectable level of human hemoglobin. A positive test is indicated with two rose-pink color bands appear, one in the test (T) zone and one in the control (C) zone. A positive result indicates that the specimen contains human hemoglobin. An invalid test is indicated where no bands appear, or a test band appears without a control band appearing. Subsequent to viewing the result, the result is communicated to the subject.

Example 2

Over-the-Counter Fecal Occult Blood Test

Alternatively to the use of a rapid test apparatus to test for the presence of blood in feces as described in Example 1, the same apparatus may be employed for in-home testing by a retail consumer. In this case, the sample acquisition is the same as described in Example 1; however, after the sample is added to the buffer and agitated, the user activates the test by twisting (if configured as illustrated in FIGS. 3A-3G) or pulling (if configured as illustrated in FIGS. 5A-5B) the base of the test apparatus. Following activation, the apparatus is set upright on a flat surface and the results of the test read, by the consumer, at the designated time. The instructions provided with the over-the-counter apparatus provide information to the consumer for reporting the results of the test to a physician.

Example 3

Apparatus for Testing for One or More Illicit Drugs

The test apparatus in this example is used to detect the the presence of recreational drugs and/or drugs of abuse, for example, cannabinoids, cocaine, methamphetamine, opiates, and phencyclidines.

A urine sample is collected from a subject, and a portion of the urine sample is introduced into the sample receiving chamber of a test apparatus as shown in FIGS. 5A-5D. The cap of the apparatus is placed on the test assembly, and tightened securely. The base of the apparatus is moved downward by pulling in a downward direction on the base. Movement of the base downward opens the valve, and allows the urine sample inside of the sample receiving chamber to flow into the test chamber in which an immunoassay test strip is diposed. The apparatus is set upright on a flat surface for at least 5 minutes. The base is then moved upward into its original position to close the valve. The immunoassay test strip is visually inspected (e.g., by the patient, by laboratory or medical personnel, or by court or law enforcement personnel) for viewing of the test and/or control lines to ascertain the presence or absence of a drug in the urine sample.

Example 4

Test Chamber Apparatus for Testing the Presence of Influenza Viruses

The detection of influenza A and influenza B viral strains can be performed using an alternative embodiment of the test apparatus. Such embodiment lacks the sampling wand (member) or comprises a swab material at the end of the sampling wand. Within the sample receiving chamber is an extraction buffer as follows: 12.5 mM Tris (pH 9.4), 32.9 mM EDTA, 1.5 mM TCEP, 0.025 mg/mL mouse IgG, and 0.025 wt % Empigen BB with 0.2 mg/mL RNase A.

A sample of nasal discharge is collected from a test subject by discharge of nasal mucus within a tissue, or by swabbing into the nasal or nasopharyngeal passageway with a sampling wand or sterile swab. The tissue, swab, or sampling wand containing the mucus sample is directly inserted into the sample receiving chamber of the apparatus, and the cap is tightened securely. The test apparatus is shaken to extract proteins from the sample by mixing with the extraction buffer that is in the sample receiving chamber. The base is moved to open the valve and allow the sample solution inside of the sample receiving chamber to flow into the test chamber. The apparatus is set upright on a flat surface for at least 10 minutes. The base is moved back into its original position to close the valve. If conducted at home, the immunoassay test results are then either read by the patient or the apparatus is shipped to a doctor's office, within 7 days of activating the apparatus, and the results read by a clinician. If the test is performed at a doctor's office, retail clinic or other medical facility, the immunoassay test strip disposed in the test chamber of the apparatus is visually inspected by a clinician, and the presence or absence of influenza A and/or influenza B is determined by the visual detection and location of a pink colored test line.

Example 5

Accelerated Stability Study

An accelerated stability study was performed to determine the stability of exemplary assay test strips within an apparatus, compared to the stability of assay strips not contained with an apparatus. The stability study was performed using an apparatus as illustrated in FIG. 1, although the results are applicable to the other apparatus embodiments described herein.

The test apparatus included 2 mL of sample buffer in the sample receiving chamber, a molecular sieve desiccant, and a test strip with hemoglobin spotted onto a test line on the test strip. The optical density (OD) was measured at the test line at various time points under different conditions. An acceptable range for the OD is between 0.015-0.025 OD for 50 ng/mL hemoglobin. Changes in OD over time indicate instability. In particular, a decrease in OD suggests protein degradation, while an increase in OD suggests microorganisin growth.

Figure 7A:
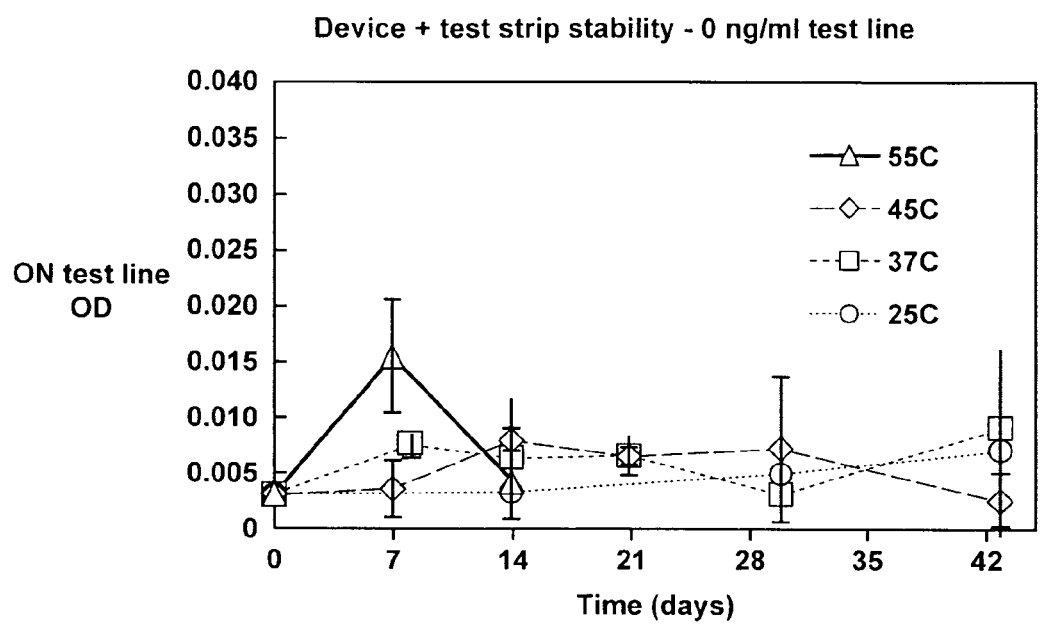
FIGS. 7A-7F are graphs showing the optical density of hemoglobin as a function of time, in days, at various temperatures, the hemoglobin deposited on an immunoassay test strip at concentrations of 50 ng/mL (FIGS. 7C-7D) or 150 ng/mL (FIGS. 7E-7F), and the immunoassay test strip placed within an apparatus as described herein (FIGS. 7A, 7C, 7E) or not within an apparatus (FIGS. 7B, 7D, 7F).
Figure 7B:
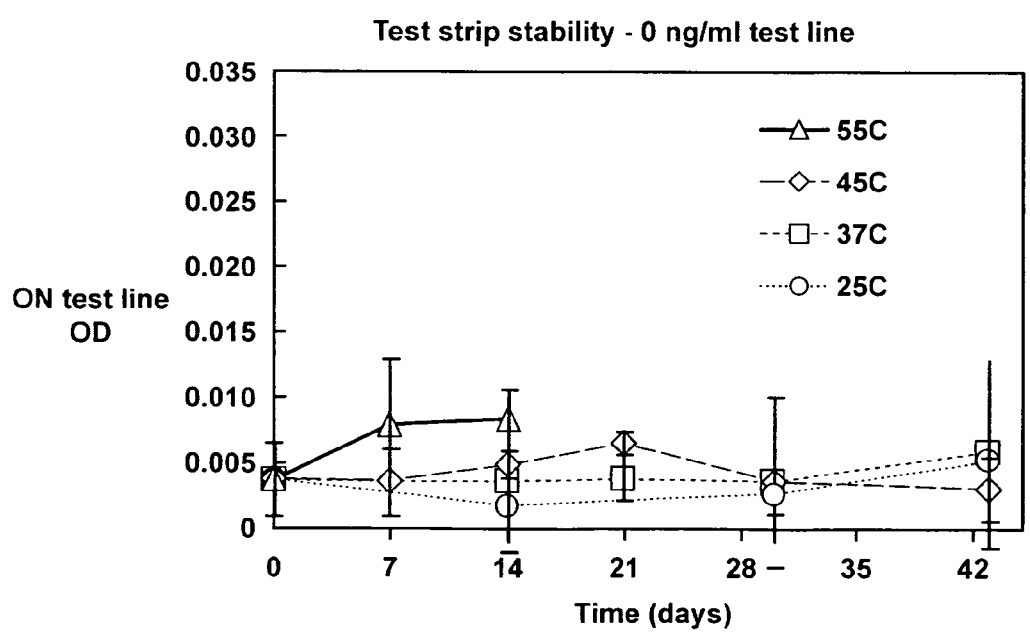
Figure 7C:
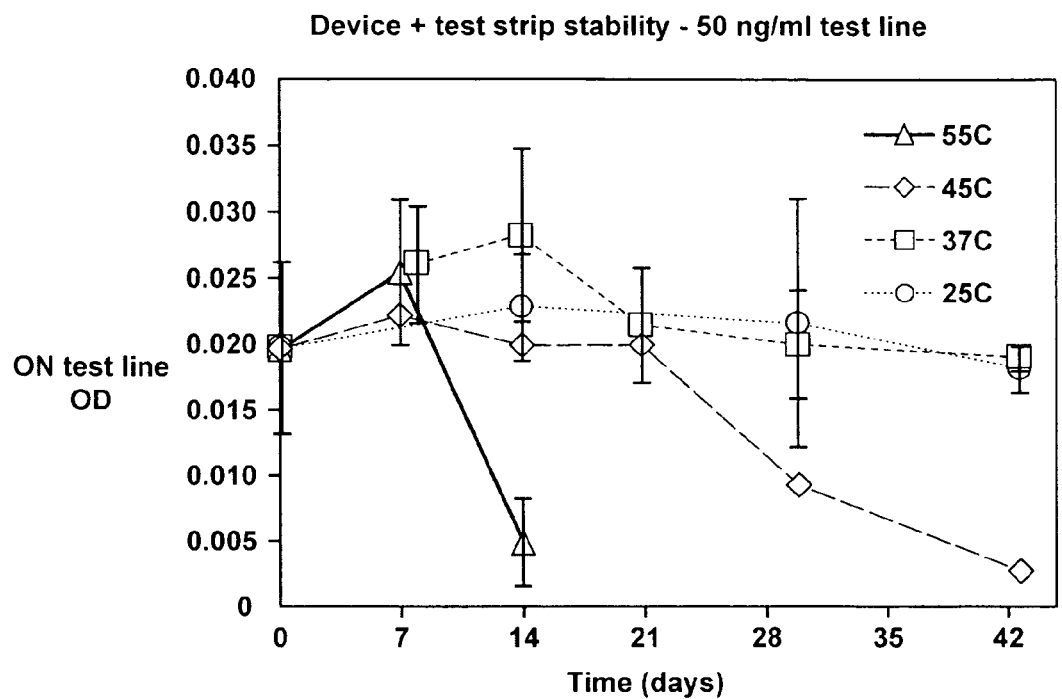
Figure 7D:
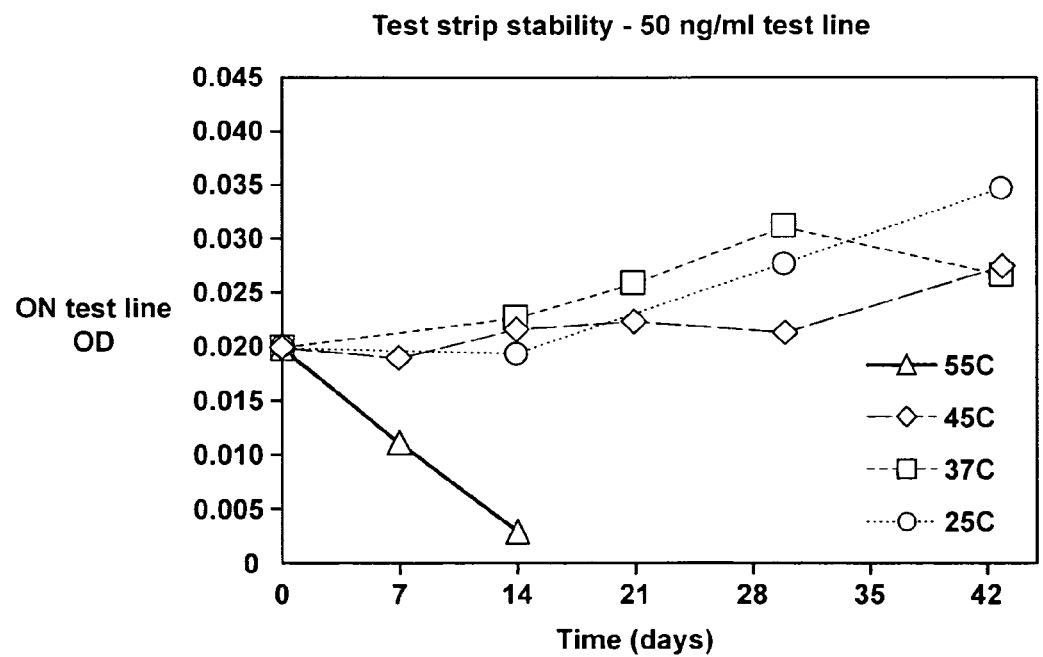
Figure 7E:
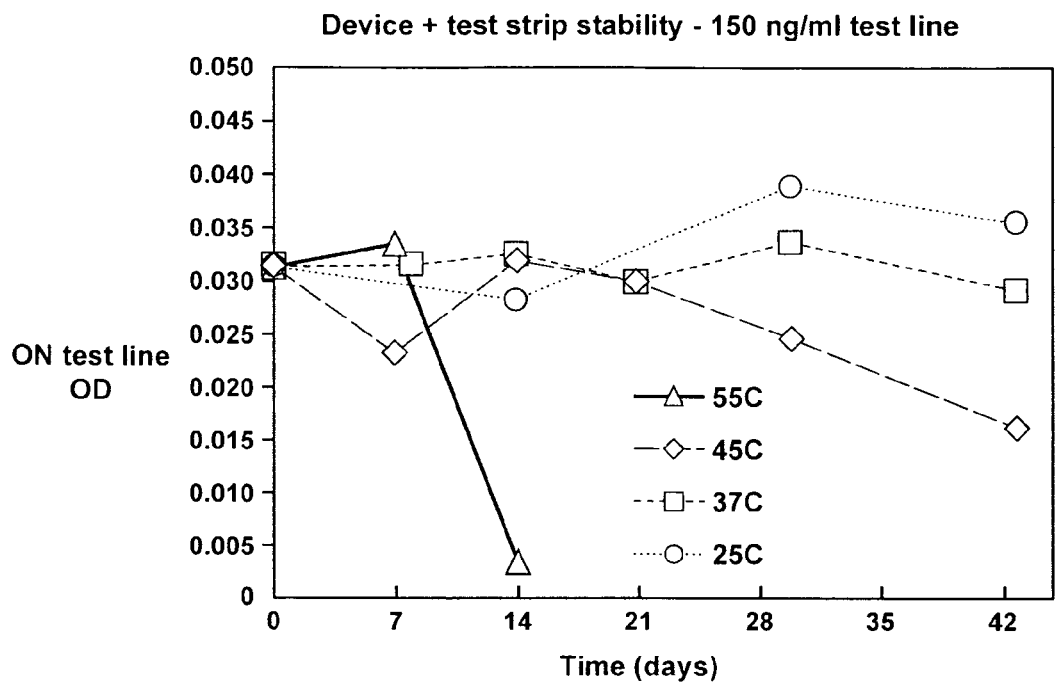
Figure 7F:
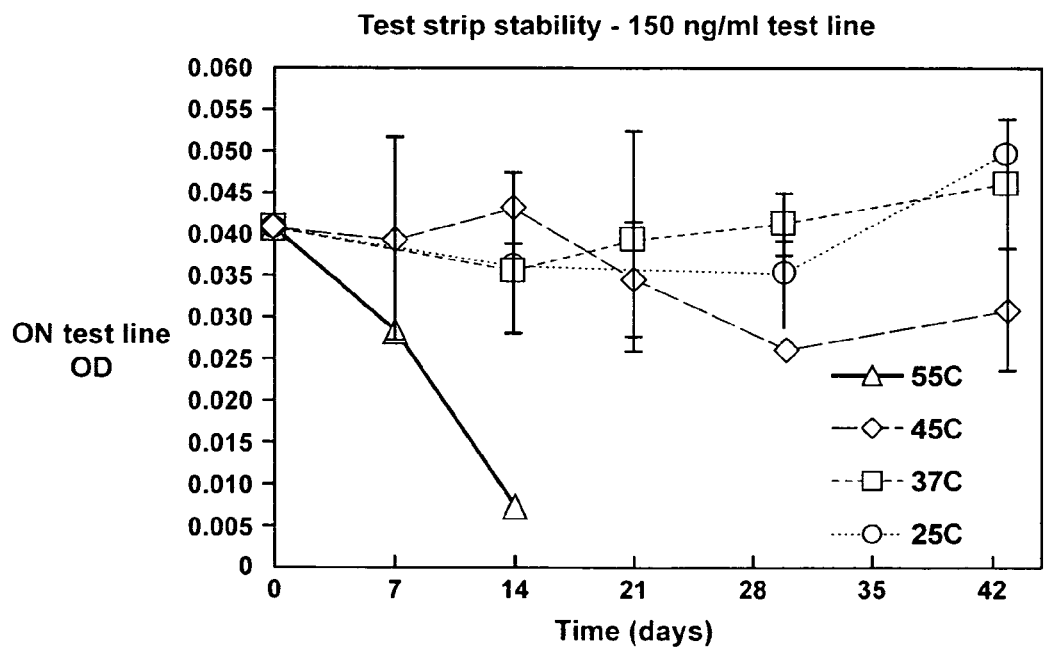

Tables 1-3 and FIGS. 7A-7F summarize the results of the accelerated stability study. Tables 1A, 2A, and 3A, and FIGS. 7A, 7C, and 7E, show OD data for strips contained within the exemplary test apparatus. Tables 1B, 2B, and 3B, and FIGS. 7B, 7D, and 7F show OD data for isolated strips that were not contained within an apparatus.

As shown in Tables 1A-1B and FIGS. 7A and 7B, test strips without hemoglobin (i.e., 0 ng/mL) were stable when contained in a test chamber of an apparatus or when not contained in an apparatus, as evidenced by the consistency in OD measurements.

TABLE 1A

Test strip in apparatus; 0 ng/ml hemoglobin (n = 10)

| | Time(days) | | | | | |
|---|---|---|---|---|---|---|
| | 0 | 7 | 14 | 21 | 30 | 43 |
| 25° C. | 0.003 | N/A | 0.003 | N/A | 0.005 | N/A |
| 37° C. | 0.003 | 0.008 | 0.006 | 0.007 | 0.003 | 0.009 |
| 45° C. | 0.003 | 0.004 | 0.008 | 0.007 | 0.007 | 0.003 |
| 55° C. | 0.003 | 0.016 | 0.004 | N/A | N/A | N/A |

TABLE 1B

Isolated test strip; 0 ng/ml hemoglobin (n = 10)

| | Time(days) | | | | | |
|---|---|---|---|---|---|---|
| | 0 | 7 | 14 | 21 | 30 | 43 |
| 25° C. | 0.004 | N/A | 0.002 | N/A | 0.003 | 0.005 |
| 37° C. | 0.004 | N/A | 0.004 | 0.004 | 0.004 | 0.006 |
| 45° C. | 0.004 | 0.004 | 0.005 | 0.007 | 0.004 | 0.003 |
| 55° C. | 0.004 | 0.008 | 0.008 | N/A | N/A | N/A |

As shown in Tables 2A-2B and in FIGS. 7C-7D, test strips with 50 ng/mL hemoglobin were more stable when contained within an apparatus, as evidence by the stable OD readings over time, particularly at higher temperatures.

TABLE 2A

Test strip in apparatus; 50 ng/ml hemoglobin (n = 10)

| | Time(days) | | | | |
|---|---|---|---|---|---|
| | 0 | 7 | 14 | 21 | 30 | 43 |
| 25° C. | 0.020 | N/A | 0.023 | N/A | 0.022 | 0.018 |
| 37° C. | 0.020 | 0.026 | 0.028 | 0.021 | 0.020 | 0.019 |
| 45° C. | 0.020 | 0.022 | 0.020 | 0.020 | 0.009 | 0.003 |
| 55° C. | 0.020 | 0.025 | 0.005 | N/A | N/A | N/A |

TABLE 2B

Isolated test strip; 50 ng/ml hemoglobin (n = 10)

| | Time(days) | | | | |
|---|---|---|---|---|---|
| | 0 | 7 | 14 | 21 | 30 | 43 |
| 25° C. | 0.020 | N/A | 0.019 | N/A | 0.028 | 0.035 |
| 37° C. | 0.020 | N/A | 0.023 | 0.026 | 0.031 | 0.027 |
| 45° C. | 0.020 | 0.019 | 0.022 | 0.022 | 0.021 | 0.027 |
| 55° C. | 0.020 | 0.011 | 0.003 | N/A | N/A | N/A |

Similarly, as shown in Tables 3A-3B and FIGS. 7E-7F, test strips with 150 ng/mL hemoglobin, were more stable when contained within a test apparatus, as evidence by the more stable OD readings over time, particularly at higher temperatures.

TABLE 3A

Test strip in apparatus; 150 ng/ml hemoglobin (n = 10)

| | Time(days) | | | | |
|---|---|---|---|---|---|
| | 0 | 7 | 14 | 21 | 30 | 43 |
| 25° C. | 0.031 | N/A | 0.028 | N/A | 0.031 | 0.036 |
| 37° C. | 0.031 | 0.032 | 0.033 | 0.030 | 0.034 | 0.029 |
| 45° C. | 0.031 | 0.023 | 0.032 | 0.030 | 0.025 | 0.016 |
| 55° C. | 0.031 | 0.034 | 0.004 | N/A | N/A | N/A |

TABLE 3B

Isolated test strip; 150 ng/ml hemoglobin (n = 10)

| | Time(days) | | | | |
|---|---|---|---|---|---|
| | 0 | 7 | 14 | 21 | 30 | 43 |
| 25° C. | 0.041 | N/A | 0.036 | N/A | 0.035 | 0.050 |
| 37° C. | 0.041 | N/A | 0.035 | 0.039 | 0.041 | 0.046 |
| 45° C. | 0.041 | 0.039 | 0.043 | 0.035 | 0.026 | 0.031 |
| 55° C. | 0.041 | 0.028 | 0.007 | N/A | N/A | N/A |

These results demonstrate that the rapid test apparatus increases the stability of a protein sample on a test strip, validating the test apparatus as a means for performing assays based on such test strips.

While a number of exemplary aspects and embodiments have been discussed above, those of skill in the art will recognize certain modifications, permutations, additions and sub-combinations thereof It is therefore intended that the following appended claims and claims hereafter introduced are interpreted to include all such modifications, permutations, additions and sub-combinations as are within their true spirit and scope.

What is claimed is:

1. An apparatus for analysis of a biological sample, comprising:
a test assembly comprising an inner wall defining a sample-receiving chamber and a median wall that together with the inner wall defines a test chamber, said test chamber containing an assay test strip, and the sample-receiving chamber and the test chamber capable of fluid communication via an opening,
wherein the median wall extends beyond a bottom portion of the inner wall into a base portion, said base portion comprising a gap into which said median wall slidably fits an assay test strip disposed in the test chamber; and such that said base is movably mounted on the test assembly, the base moveable between a closed position and an open position to achieve movement of a valve dimensioned for engagement with said opening, which controls fluid flow from the sample-receiving chamber, via the opening, to the test chamber,
wherein said base further comprises one or more guide pins that enrage with one or more grooves in the median wall and thereby control the extent of movement of said valve and prevent the base from moving beyond a preselected amount.

2. The apparatus of claim 1, wherein the groove is one or more grooves are dimensioned to achieve movement of the base in a radial direction.

3. The apparatus of claim 1, wherein the one or more grooves are dimensioned to achieve movement of the base in a longitudinal direction.

4. The apparatus of claim 1, wherein the one or more grooves comprise one or more narrowing regions.

5. The apparatus of claim 1, further comprising one or more sub-chambers defined by lateral wall members connecting said inner wall and said median wall.

6. The apparatus of claim 1, further comprising a cap with an integral sampling wand.

7. The apparatus of claim 1, wherein the assay test strip is housed in a strip holder sleeve.

8. The apparatus of claim 7, wherein the strip holder sleeve has a tip adapted to reduce formation of bubbles when in contact with a liquid flowing into the test strip.

9. The apparatus of claim 5, wherein a desiccant is disposed in the one or more sub-chambers.

10. The apparatus of claim 5, wherein an assay test strip is disposed in the one or more sub-chambers.

11. The apparatus of claim 1, wherein the sample is a solid or semi-solid sample.

12. The apparatus of claim 11, wherein the sample is a fecal sample.

13. The apparatus of claim 1, wherein the assay test strip comprises at least one antibody.

14. The apparatus of claim 1, comprising a transparent portion in the test assembly for viewing the assay test strip.

15. A kit of parts comprising the apparatus of claim 1 and instructions for use.

16. A kit of parts comprising the apparatus of claim 1, instructions for use, and a label for affixing to the apparatus.

17. An apparatus for detection of an analyte of interest in a biological sample, comprising:
a test assembly comprising an inner wall defining a sample-receiving chamber and a median wall that together with the inner wall defines a test chamber, the sample-receiving chamber and the test chamber capable of fluid communication via an opening, and an assay test strip assembly comprised of comprising a first assay test strip and a strip holder sleeve;

wherein said median wall extends beyond a bottom portion of said inner wall into a base portion said base portion comprising a gap into which said median wall slidably fits, such that said base is movably mounted on the test assembly, the base moveable between a closed position and an open position to achieve movement of a valve dimensioned for engagement with the said opening which controls fluid flow from the sample-receiving chamber, via the opening, to the test chamber, wherein said base further comprises one or more guide pins that engage with one or more grooves in the median wall and thereby control the extent of movement of said valve and prevent the base from moving beyond a preselected amount.

18. The apparatus of claim 17, further comprising one or more structures formed on a wall of the test chamber for securing the assay test strip in the test chamber.

19. The apparatus of claim 17, further comprising one or more structures formed on an external surface of the strip holder sleeve for securing the assay test strip in the test chamber.

20. The apparatus of claim 17, further comprising one or more sub-chambers.

21. The apparatus of claim 20, wherein the one or more sub-chambers comprises a desiccant.

22. The apparatus of claim 21, wherein the desiccant is a film desiccant.

23. The apparatus of claim 20, wherein the one or more sub-chambers comprises a second assay test strip, for detection of the same or different analyte of interest.

24. The apparatus of claim 17, further comprising a cap with an integral sampling wand.

25. The apparatus of claim 17, wherein the strip holder sleeve has a tip adapted to reduce formation of bubbles when in contact with a liquid flowing into the test strip.

* * * * *

UNITED STATES PATENT AND TRADEMARK OFFICE
CERTIFICATE OF CORRECTION

PATENT NO.        : 7,794,656 B2
APPLICATION NO.   : 12/150148
DATED             : September 14, 2010
INVENTOR(S)       : Greg Liang and Kevin J. Kirby Page 1 of 1

It is certified that error appears in the above-identified patent and that said Letters Patent is hereby corrected as shown below:

Col. 22, line 13; Claim 1, line 12 thereof: insert a --,-- after "fits".

Col. 22, lines 13-14; Claim 1, line 12-13 thereof: after "slidably fits" delete the phrase "an assay test strip disposed in the test camber; and".

Col. 22, line 22; Claim 1, line 21 thereof: Change "enrage" to --engage--.

Col. 22, line 26; Claim 2, line 1 thereof: delete "groove is".

Col. 23, line 2; Claim 17, line 8 thereof: delete "comprised of".

Col. 23, line 12; Claim 17, line 16 thereof: delete "the" and insert a --,-- after "opening".

Signed and Sealed this
Eleventh Day of January, 2011

David J. Kappos
*Director of the United States Patent and Trademark Office*